US012768719B2

(12) United States Patent
Morgan, III et al.

(10) Patent No.: US 12,768,719 B2
(45) Date of Patent: Oct. 20, 2026

(54) PROBE FOR MEASURING OPTICAL PROPERTIES OF LIQUIDS

(71) Applicants: Ranzy Morgan, III, La Marque, TX (US); Sandra Morgan, La Marque, TX (US); Kai Xin, Troy, NY (US); David Gibson, Slingerlands, NY (US)

(72) Inventors: Ranzy Morgan, III, La Marque, TX (US); Sandra Morgan, La Marque, TX (US); Kai Xin, Troy, NY (US); David Gibson, Slingerlands, NY (US)

(73) Assignee: Choice Analytical, Inc., La Marque, TX (US)

( * ) Notice: Subject to any disclaimer, the term of this patent is extended or adjusted under 35 U.S.C. 154(b) by 73 days.

(21) Appl. No.: 18/752,576

(22) Filed: Jun. 24, 2024

(65) Prior Publication Data

US 2025/0027815 A1 Jan. 23, 2025

Related U.S. Application Data

(63) Continuation-in-part of application No. 18/176,092, filed on Feb. 28, 2023, now Pat. No. 12,216,007, (Continued)

(51) Int. Cl.
*G01J 3/42* (2006.01)
*G01J 3/28* (2006.01)
(Continued)

(52) U.S. Cl.
CPC ............... *G01J 3/42* (2013.01); *G01J 3/2803* (2013.01); *G01N 21/01* (2013.01); *G01N 21/59* (2013.01); *G01N 33/22* (2013.01); *G01N 33/2888* (2013.01)

(58) Field of Classification Search
CPC .......... G01J 3/42; G01J 3/2803; G01N 21/01; G01N 21/59; G01N 33/22; G01N 33/2888
See application file for complete search history.

(56) References Cited

U.S. PATENT DOCUMENTS 4,762,413 A 8/1988 Namba et al.
5,007,733 A 4/1991 Laurent et al.
(Continued)

OTHER PUBLICATIONS

A Good Choice for Haze Determination Achieves ASTM D8148-17 Designation, Petro Industry News, Jan. 5, 2018, available at https://www.petro-online.com/news/analytical-instrumentation/11/choice-analytical/a-good-choice-for-haze-determination-achieves-astm-d8148-17-designation/44698, 2 Pages (p. 1, para 1; p. 2, para 2-3).
(Continued)

*Primary Examiner* — Jamil Ahmed
(74) *Attorney, Agent, or Firm* — Alberto Q. Amatong, Jr.; Amatong McCoy LLC

(57) ABSTRACT

The present disclosure provides for a system for measuring optical properties of liquid samples. The system includes a housing having a multi-wavelength light source, a collimator, a beam-splitter, and a light sensor. A probe extends from the housing, The probe includes a sample inlet configured to receive a liquid sample. The multi-wavelength light source is positioned to direct light to the collimator, the collimator is positioned to direct light to the beam-splitter, the beam-splitter is positioned to direct light to the probe, and the light sensor is positioned to receive light transmitted through the probe.

25 Claims, 20 Drawing Sheets

Related U.S. Application Data which is a continuation of application No. 17/188,062, filed on Mar. 1, 2021, now Pat. No. 11,619,549, which is a continuation of application No. 16/396,287, filed on Apr. 26, 2019, now Pat. No. 10,976,201.

(60) Provisional application No. 63/510,017, filed on Jun. 23, 2023, provisional application No. 62/745,187, filed on Oct. 12, 2018, provisional application No. 62/689,726, filed on Jun. 25, 2018.

(51) Int. Cl.

| | |
|---|---|
| ***G01N 21/01*** | (2006.01) |
| ***G01N 21/59*** | (2006.01) |
| ***G01N 33/22*** | (2006.01) |
| ***G01N 33/28*** | (2006.01) |

(56) References Cited

U.S. PATENT DOCUMENTS

| | | | | |
|---|---|---|---|---|
| 5,825,478 | A | 10/1998 | Wilcox et al. | |
| 5,969,814 | A | 10/1999 | Barber et al. | |
| 6,825,921 | B1 | 11/2004 | Modlin et al. | |
| 8,248,255 | B2 | 8/2012 | Tzidon et al. | |
| 9,041,920 | B2 | 5/2015 | Mander et al. | |
| 9,448,112 | B2 | 9/2016 | Greer et al. | |
| 9,869,636 | B2 | 1/2018 | Mander et al. | |
| 10,976,201 | B2 | 4/2021 | Morgan | |
| 2002/0042142 | A1 | 4/2002 | Kawamura | |
| 2003/0058450 | A1 | 3/2003 | Matthew et al. | |
| 2003/0127609 | A1* | 7/2003 | El-Hage | G01N 21/6452 250/574 |
| 2005/0095716 | A1 | 5/2005 | Wollenberg et al. | |
| 2006/0144126 | A1 | 7/2006 | O'Brien et al. | |
| 2009/0098022 | A1 | 4/2009 | Tokhtuev et al. | |
| 2010/0202726 | A1 | 8/2010 | Egalon | |
| 2011/0083995 | A1 | 4/2011 | Gleeson et al. | |
| 2011/0255745 | A1 | 10/2011 | Hodder et al. | |
| 2012/0170023 | A1 | 7/2012 | Szobota et al. | |
| 2013/0020480 | A1* | 1/2013 | Ford | G01J 3/4338 250/256 |
| 2014/0233015 | A1 | 8/2014 | Mander et al. | |
| 2014/0234952 | A1 | 8/2014 | Moore | |
| 2015/0260641 | A1 | 9/2015 | Sperling et al. | |
| 2015/0276594 | A1 | 10/2015 | Johnson et al. | |
| 2016/0040985 | A1 | 2/2016 | Nagai et al. | |
| 2016/0193146 | A1 | 7/2016 | Bromley | |
| 2017/0199079 | A1 | 7/2017 | Takebe et al. | |
| 2018/0059006 | A1 | 3/2018 | Fritchie et al. | |
| 2019/0310193 | A1 | 10/2019 | Scardina et al. | |
| 2020/0132593 | A1 | 4/2020 | Schwarz | |
| 2020/0209208 | A1 | 7/2020 | Li et al. | |

OTHER PUBLICATIONS

Anonymous: "ASTM D8148 takes haze and clarity ratings to the modern age", Petrochemical Chemical & Energy, Retrieved from the Internet on Aug. 6, 2025, https://www.petro-online.com/news/analytical-instrumentation/11/choice-analytical/astm-d8148-takes-haze-and-clarity-ratings-to-the-modern-age/50198 (7 pages).

Anonymous: "Choice Analytical Inc. Receives ASTM D8148-17 Method", Fuels Market News, Jan. 4, 2018, Retrieved from the Internet on Aug. 6, 2025, https://fuelsmarketnews.com/choice-analytical-inc-receives-astm-d8148-17-method/?utm_source=chatgpt.com (5 pages).

Anonymous: "Standard Terminology Relating to Petroleum Products, Liquid Fuels, and Lubricants", ASTM D4175-24e1, Nov. 19, 2024, Advancing Standards Transforming Markets, Retrieved from the Internet on Aug. 15, 2025,https://store.astm.org/d4175-24e01.html (3 pages).

Anonymous: "Standard Test Method for ASTM Color of Petroleum Products (ASTM Color Scale)", ASTM D1500-24, Mar. 26, 2024, Advancing Standards Transforming Markets, Retrieved from the Internet on Aug. 15, 2025, https://store.astm.org/d1500-24.html (3 pages).

Anonymous: "Standard Test Method for Color of Clear Liquids (Platinum-Cobalt Scale)", ASTM D1209-25, Jan. 16, 2025, Advancing Standards Transforming Markets, Retrieved from the Internet on Aug. 15, 2025, https://store.astm.org/d1209-25.html (4 pages).

Anonymous: "Standard Test Method for Color of Liquids Using Tristimulus Colorimetry", ASTM D5386-24, May 9, 2024, Advancing Standards Transforming Markets, Retrieved from the Internet on Aug. 15, 2025, https://store.astm.org/d5386-24.html (3 pages).

Anonymous: "Standard Test Method for Color of Petroleum Products by the Automatic Tristimulus Method", ASTM D6045-20, Jun. 15, 2020, Advancing Standards Transforming Markets, Retrieved from the Internet on Aug. 15, 2025, https://store.astm.org/d6045-20.html (3 pages).

Anonymous: "Standard Test Method for Free Water and Particulate Contamination in Distillate Fuels (Visual Inspection Procedures)", ASTM D4176-22e1, Jun. 30, 2025, Advancing Standards Transforming Markets, Retrieved from the Internet on Aug. 15, 2025, https://store.astm.org/d4176-22e01.html (3 pages).

Anonymous: "Standard Test Method for Haze and Luminous Transmittance of Transparent Plastics", ASTM D1003-21, Jun. 7, 2021, Advancing Standards Transforming Markets, Retrieved from the Internet on Aug. 15, 2025, https://store.astm.org/d1003-21.html (4 pages).

Anonymous: "Standard Test Method for Saybolt Color of Petroleum Products (Saybolt Chromometer Method)", ASTM D156-23, Oct. 6, 2023, Advancing Standards Transforming Markets, Retrieved from the Internet on Aug. 15, 2025, https://store.astm.org/d0156-23.html (3 pages).

Anonymous: "Standard Test Method for Spectroscopic Determination of Haze in Fuels", ASTM International, Designation: D8148-22, Apr. 2022 (9 pages).

International Search Report and Written Opinion mailed Jul. 26, 2019 (issued in PCT Application No. PCT/US2019/029403) [15 pages].

Lopes, Shailesh; Chapman, Rick; Gomez, John, and Westbrook, Steve; "Evaluation of Diesel Fuel Haze Resulting from Water Content", Jan. 2022, CRC Report No. 675, Alpharetta, GA (13 pages).

Lynch, Tom and Morgan, Ranzy; "Bringing Clarity and Haze Ratings into the Modern World—ASTM D8148 Provides the Perfect Solution", Petro Industry News, Aug./Sep. (3 pages).

Shah, Raj Dr.; Forester, David; and Przyborowski, Alexandra, "Recent Advances in Test Method Development, and Instrumentation Used for Testing Diesel Fuel", Petro Industry News, (3 pages).

* cited by examiner

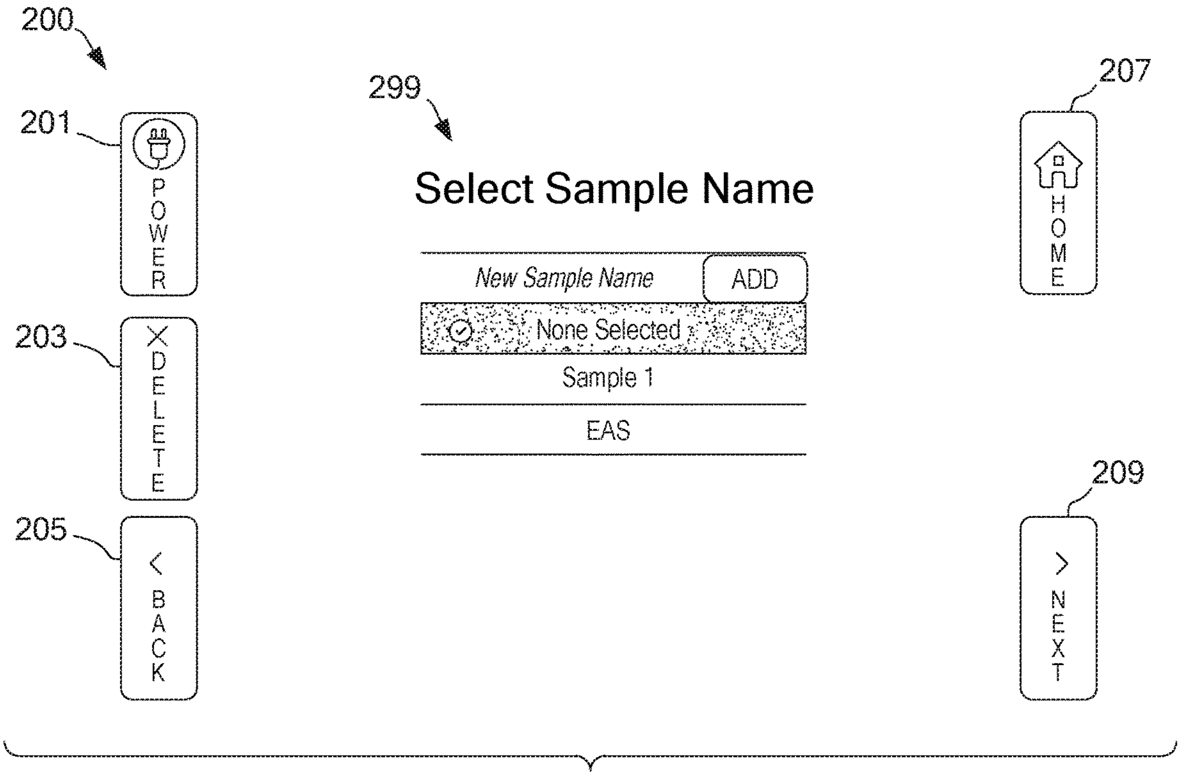
FIG. 21
FIG. 22
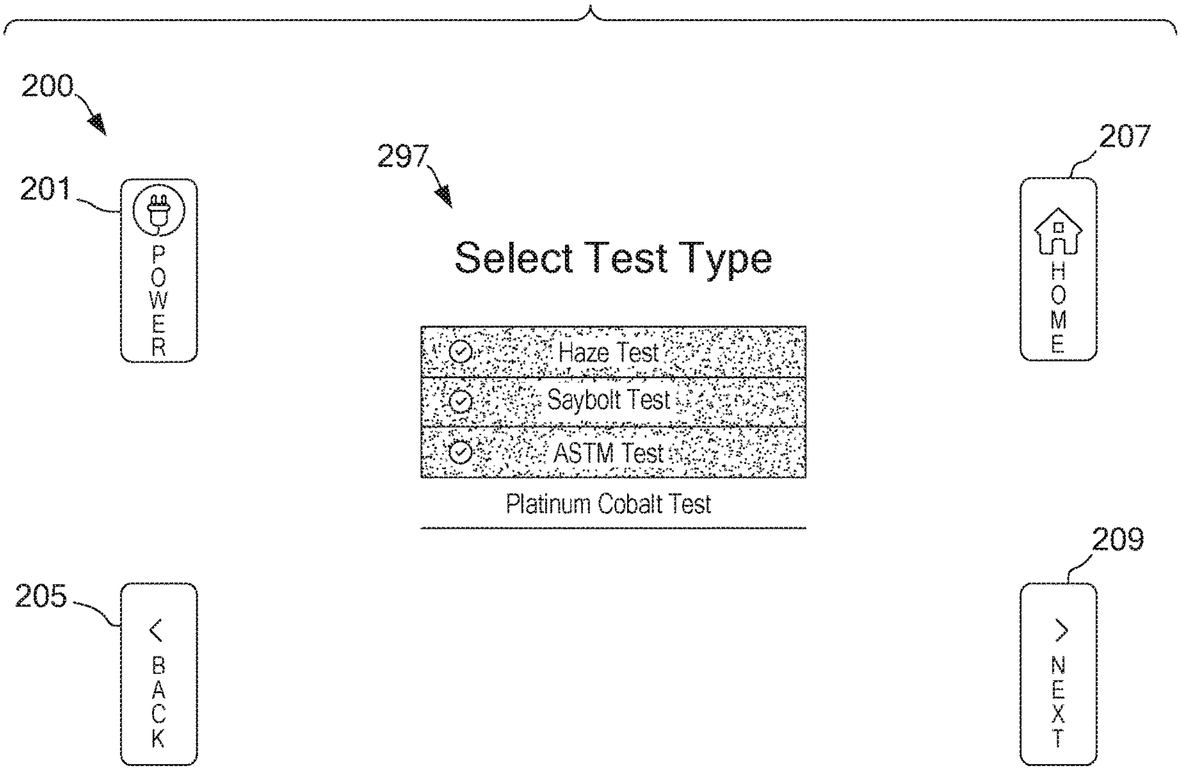

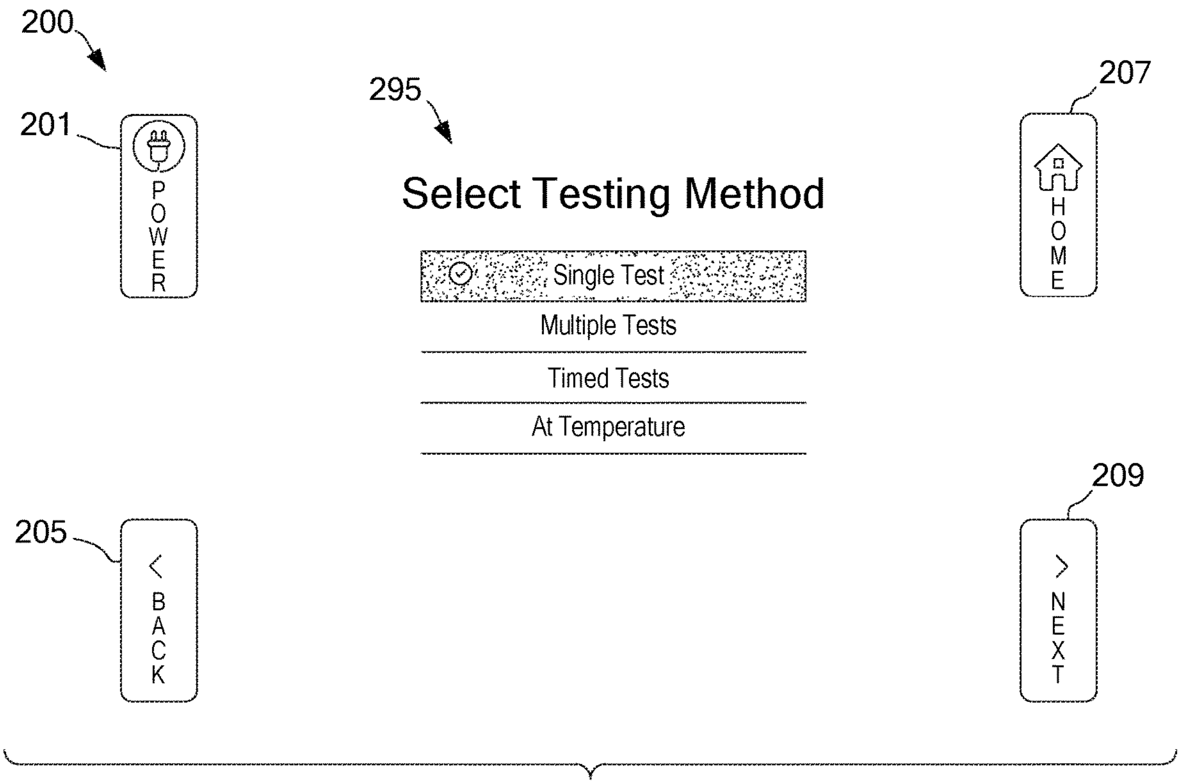
FIG. 23
FIG. 24
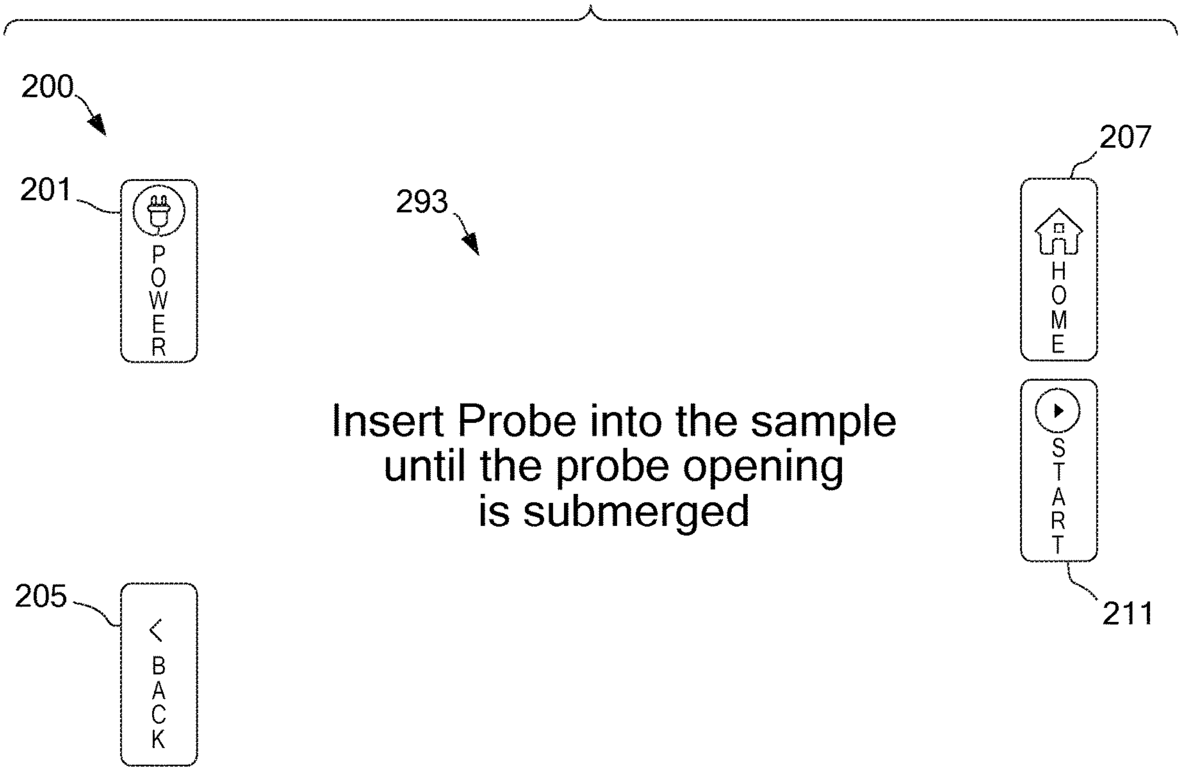

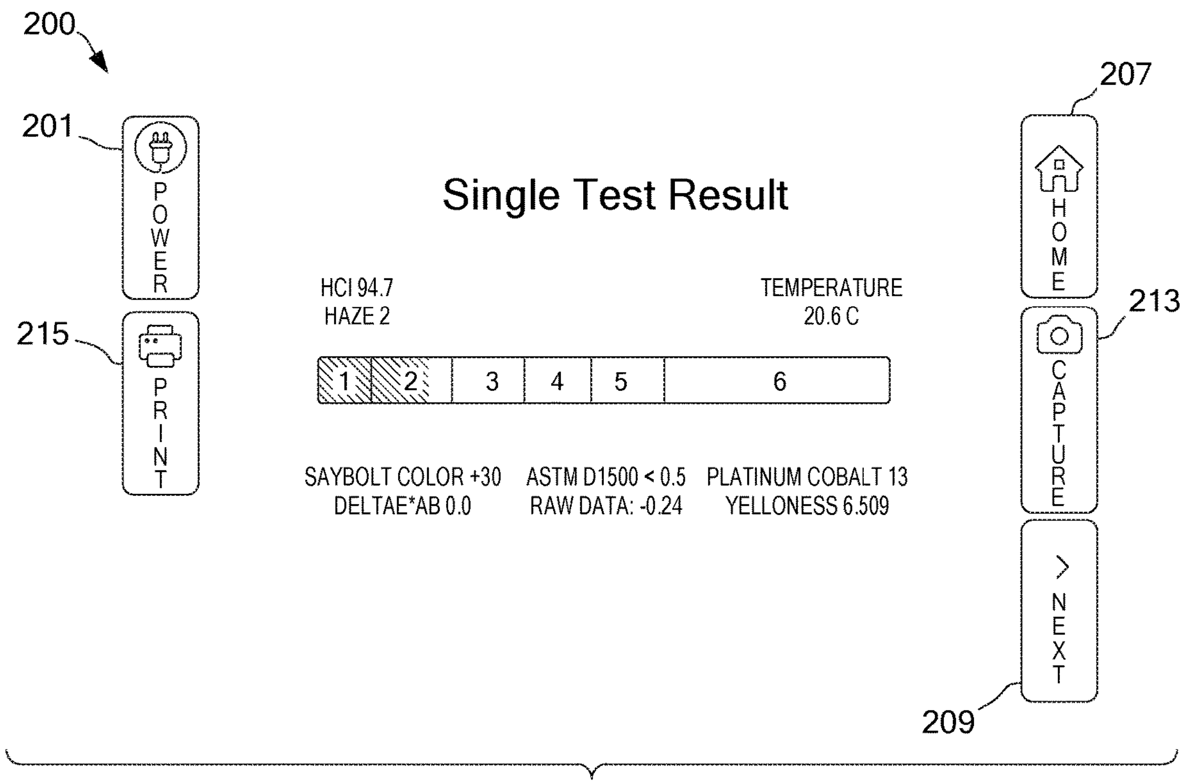
FIG. 25
FIG. 26
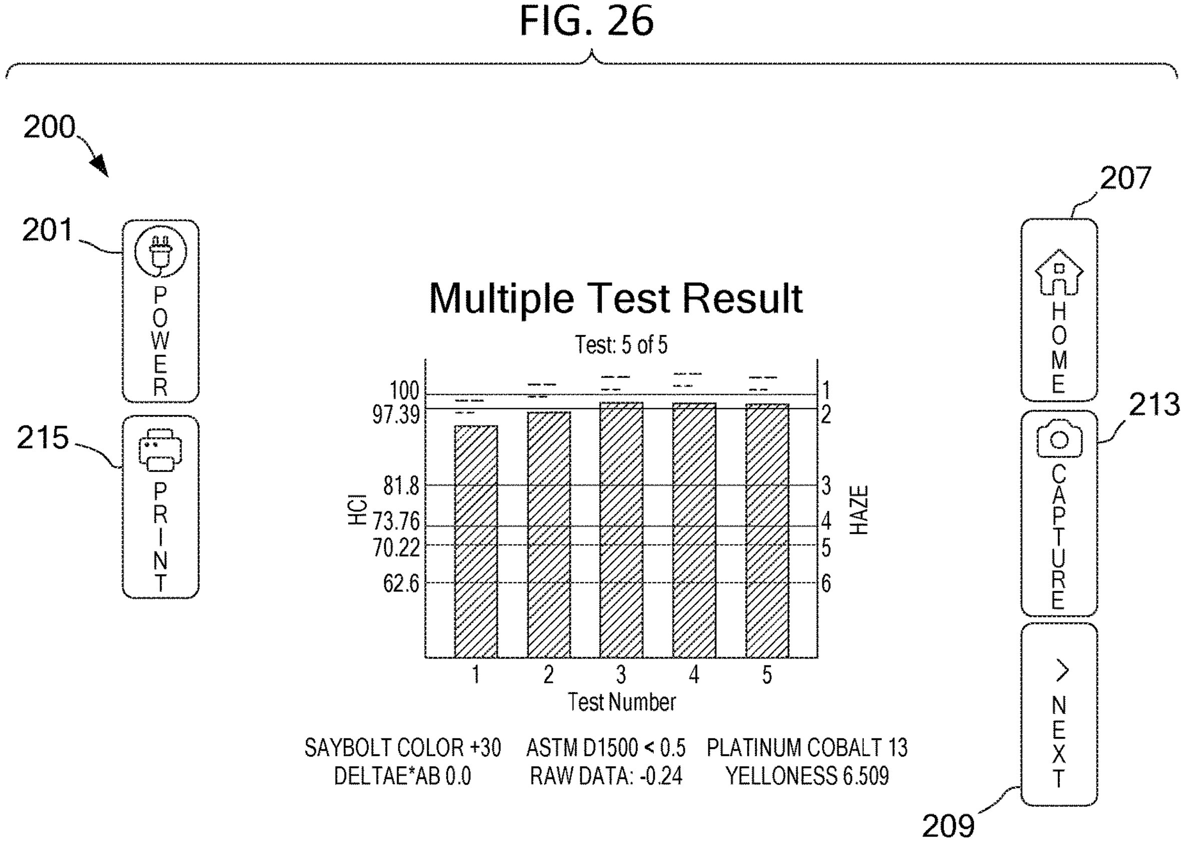

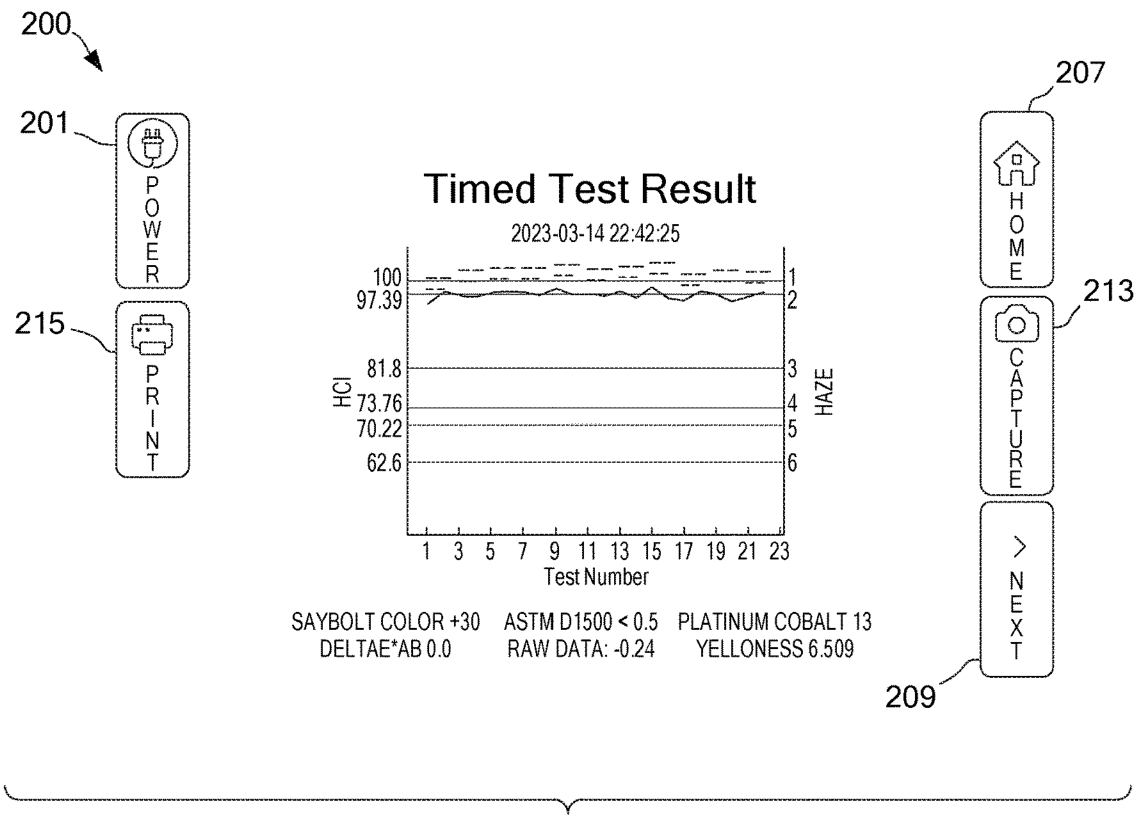
FIG. 27
FIG. 28
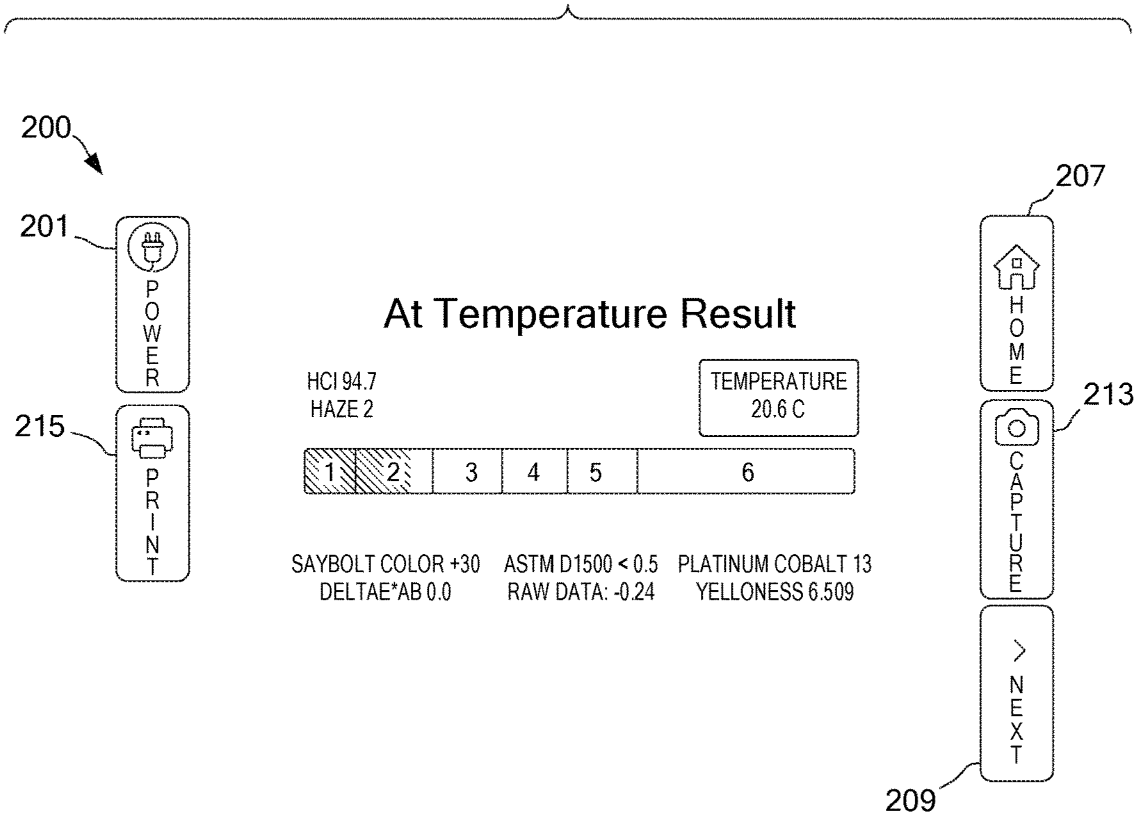

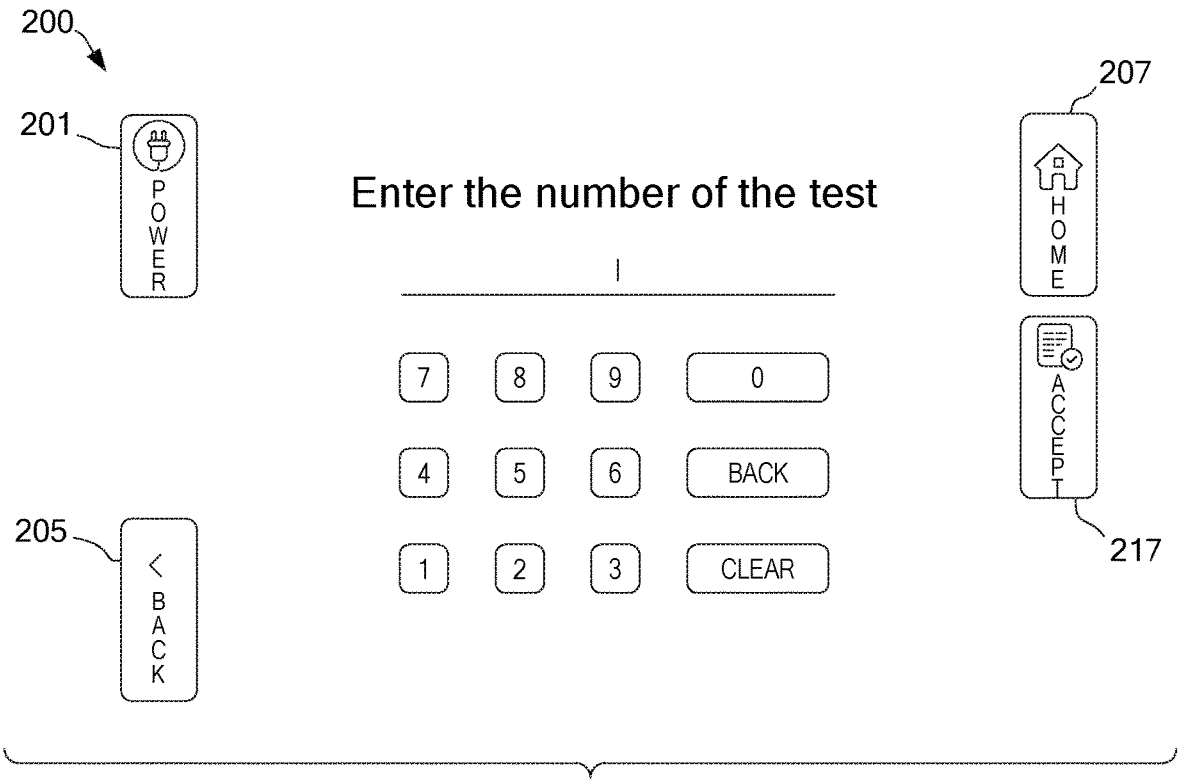
FIG. 29
FIG. 30
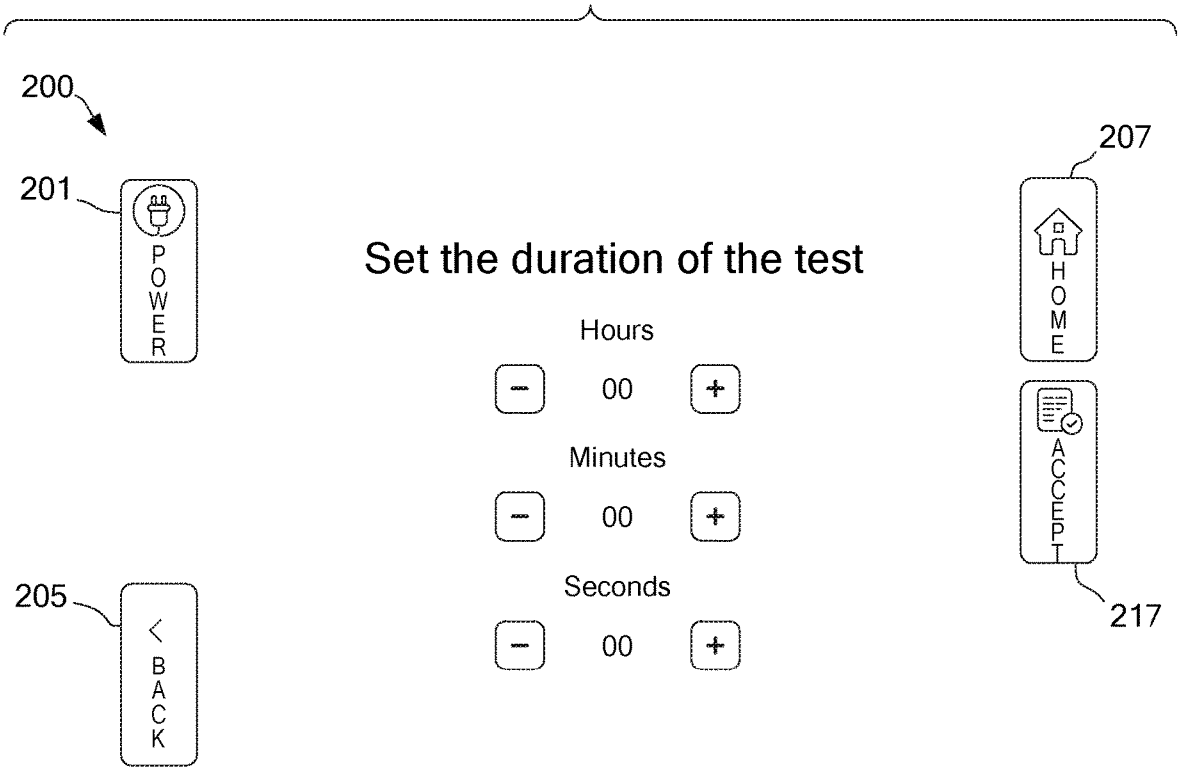

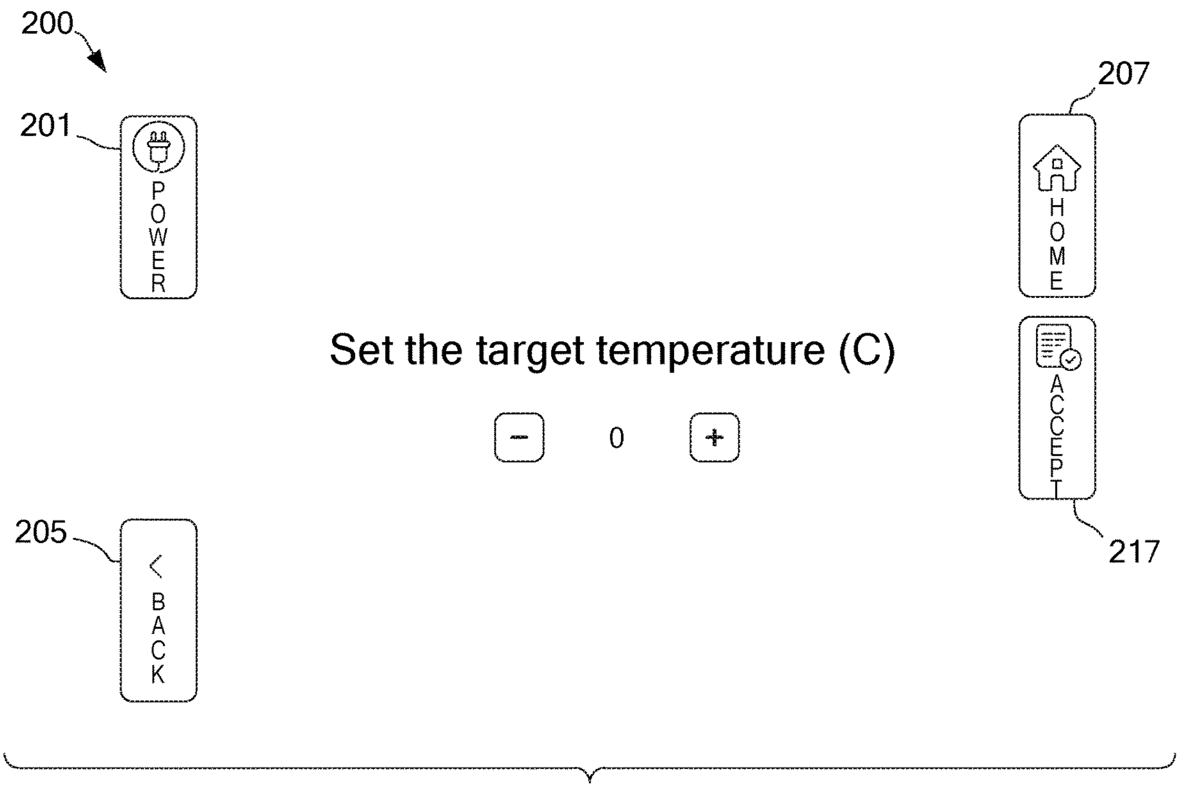
FIG. 31
FIG. 32
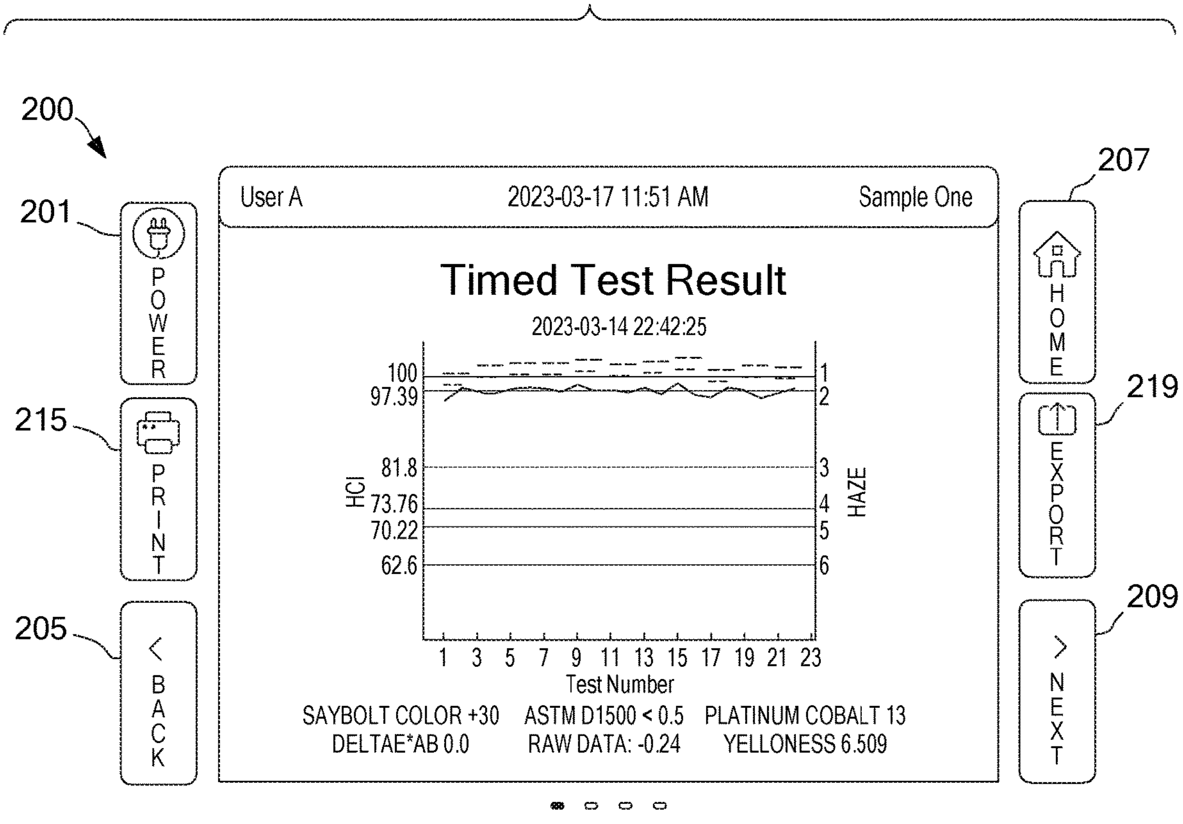

PROBE FOR MEASURING OPTICAL PROPERTIES OF LIQUIDS

CROSS-REFERENCE TO RELATED APPLICATIONS

The present application claims the benefit of U.S. Provisional Patent Application No. 63/510,017, having a filing date of Jun. 23, 2023, the entirety of which is incorporated herein by reference. The present application is also a Continuation-in-part of U.S. patent application Ser. No. 18/176,092 (pending), having a filing date of Feb. 28, 2023, the entirety of which is incorporated herein by reference; which is a Continuation of U.S. Pat. No. 11,619,549 (issued), having a filing date of Mar. 1, 2021, the entirety of which is incorporated herein by reference; which is a Continuation of U.S. Pat. No. 10,976,201 (issued), filed on Apr. 26, 2019, the entirety of which is incorporated herein by reference; which claims the benefit of U.S. Provisional Patent Application No. 62/689,726, filed on Jun. 25, 2018, the entirety of which is incorporated herein by reference, and also claims the benefit of U.S. Provisional Patent Application No. 62/745,187, filed on Oct. 12, 2018, the entirety of which is incorporated herein by reference.

FIELD

The present application relates to systems and methods for measuring optical properties of liquids, and subsystems and components thereof and therefor, and their operation.

BACKGROUND

Certain liquids, such as petroleum-based fuels, must meet optical standards and specifications to confirm quality and lack of water and/or particulates within the liquids. Cloudiness and/or haziness in a fuel, which may be caused by the presence of suspended solid particulates and/or water within the fuel, can lead to the fuel not meeting the required optical specifications.

The determination of optical properties, such as haze, clarity, and color allows the quality of petroleum-based fluids, such as fuels and lubricants, to be assessed. Typically, such properties are determined by subjective techniques. For example, the determination of haze in fuels has typically involved the use of subjective, visual techniques, such as that defined by ASTM D4176, Procedure 2. When measurement of optical properties of liquids is reliant upon subjective visual techniques, results vary with operator and lighting conditions.

Current methods for determining the optical properties of certain fuel samples include visual comparison to a standard, which can lead to variations in results. One current method is using bench-top analyzers, which depend on calibration and are sensitive to sample cup properties and other factors. Often, optical property measurement methods require the use of large equipment that is not easily transported, such that samples are analyzed at a remote location rather than on-site where the sample is taken, causing time delays and increasing the risk of errors.

There is a need in the fuel industry for an easy-to-use, hand-held instrument to measure the optical properties of such liquids both quickly and accurately to ensure compliance with standards. There is a need in the fuel industry for a hand-held instrument to measure the optical properties of such liquids at an on-site location (i.e., the location where the sample is taken) rather than a remote lab.

SUMMARY

Some embodiments of the present disclosure include a system for measuring optical properties of liquid samples. The system includes a sample inlet, at least one multi-wavelength light source, at least one collimating optical chain, at least one beam-splitter, and at least one light sensor.

Some embodiments of the present disclosure include a method for measuring an optical property of a fluid environment (e.g., liquid or gas) that entails directing a transmitted light through a target environment or an intact and in-situ portion thereof (e.g., a sample) and receiving the directed transmitted light for measurement of the optical property. The system for performing the measurement includes a light source operable to generate and/or a transmit light, and a probe portion adapted for insertion or immersion in the target fluid environment. The probe portion includes a housing for accommodating a light pathway or travel of the transmitted light therethrough, and the housing includes a space that intermediates a proximal (device handle or dry end) and a distal end immersible in the target environment. The system, probe or probe section is configured to include a continuous, solid body with a space intermediate the proximal end and distal end. The space is disposed and configured so as to be substantially in fluid communication with the remainder of the target environment (the remaining volume) and generally in equilibrium therewith. The probe or housing is further configured such that the light path is directed within the housing and through the space, and outside of the probe portion in the manual or dry end. The manual or dry end may house electronics, a central processing unit (CPU), and/or data storage for the optical measurement system. In some embodiments, the space is insertable with the probe portion in the target environment so that the fluid environment occupies the space and, in this way, provides the device or probe a portion or sample of the environment that is spatially and temporally maintained within the target environment during measurement (i.e., when the transmitted light is directed therethrough). In further embodiments, the "sampling space" is provided as or with a window disposed in the housing that is open to and in fluid communication with the target environment outside of the probe portion. In some embodiments, the space is sufficiently sized and configured to readily allow (draw) the fluid therein upon the inserted probe portion displacing fluid in the environment. Care may be taken to minimize disturbance of, and energy transfer with, the fluid environment as may be desirable for measurement purposes.

Another embodiment of the present disclosure includes a spectroscopy method for measuring optical properties of liquid samples. The method includes providing a sample inlet, providing at least one multi-wavelength light source, providing at least one collimating optical chain disposed between the light source and the sample inlet to collimate the light, providing at least one beam-splitter disposed between the light source and the sample inlet to direct the light, and providing at least one sensor to measure the intensity of the light.

Another embodiment of the present disclosure includes a system for measuring optical properties of liquid samples. The system includes a housing. The housing includes or houses a multi-wavelength light source, a collimator, a beam-splitter, and a light sensor. The system includes a probe extending from the housing. The probe includes a sample inlet configured to receive a liquid sample. The multi-wavelength light source is positioned to direct light to the collimator, the collimator is positioned to direct light to the beam-splitter, the beam-splitter is positioned to direct light to the probe, and the light sensor is positioned to receive light transmitted through the probe.

Another embodiment of the present disclosure includes an apparatus for measuring an optical property of a liquid target. The apparatus includes a housing, a collimator supported by the housing, and a beam splitter supported by the housing in optical communication with the collimator.

Another embodiment of the present disclosure includes an apparatus for measuring an optical property of a liquid target. The apparatus includes a housing including a light source and an optical property measuring mechanism. A probe portion extends from the housing and includes a sampler to contact the liquid target.

Another embodiment of the present disclosure includes a method of measuring an optical property of a target liquid. The method includes providing a container of the target liquid, and providing a housing supporting a spectroscopy-based mechanism for measuring the optical property. The housing includes a probe portion having a sampler for contacting a target liquid. The method includes inserting the probe portion into said container such that the probe receives said liquid target. The method includes operating the measuring mechanism, including communicating light to said received liquid target to measure the optical property.

Another embodiment of the present disclosure includes a method of measuring optical properties of a liquid in a local environment. The method includes immersing at least a portion of a probe in the liquid within the local environment such that a sample inlet of the probe is surrounded by the liquid within the local environment and at least a portion of the liquid enters into the sample inlet. The method includes, with the portion of the probe immersed in the liquid within the local environment, transmitting a light along a path within the probe and through a portion of the liquid in the sample inlet and receiving the light at a first sensor. The method includes, with the portion of the probe immersed in the liquid within the local environment, measuring at least one property of the light with the first sensor. The method includes determining at least one property of the liquid using the at least one property of the light.

BRIEF DESCRIPTION OF THE DRAWINGS

So that the manner in which the features and advantages of the systems and methods of the present disclosure may be understood in more detail, a more particular description briefly summarized above may be had by reference to the embodiments thereof which are illustrated in the appended drawings that form a part of this specification. It is to be noted, however, that the drawings illustrate only various exemplary embodiments and are therefore not to be considered limiting of the disclosed concepts as it may include other effective embodiments as well.

FIG. 21 depicts a software-based graphical user interface for selecting a sample name during testing of samples in accordance with embodiments of the present disclosure.

FIG. 22 depicts a software-based graphical user interface for selecting a test type during testing of samples in accordance with embodiments of the present disclosure.

FIG. 23 depicts a software-based graphical user interface for selecting a testing method during testing of samples in accordance with embodiments of the present disclosure.

FIG. 24 depicts a software-based graphical user interface showing a prompt for the user to inserts the probe into the sample in accordance with embodiments of the present disclosure.

FIG. 25 depicts a software-based graphical user interface presenting a single test result during testing of a sample in accordance with embodiments of the present disclosure.

FIG. 26 depicts a software-based graphical user interface presenting multiple test results during testing of multiple samples in accordance with embodiments of the present disclosure.

FIG. 27 depicts a software-based graphical user interface presenting a timed test result during testing of a sample in accordance with embodiments of the present disclosure.

FIG. 28 depicts a software-based graphical user interface presenting an at-temperature test result during testing of a sample in accordance with embodiments of the present disclosure.

FIG. 29 depicts a software-based graphical user interface for entering a test number during testing of a sample in accordance with embodiments of the present disclosure.

FIG. 30 depicts a software-based graphical user interface for setting a duration of a test during testing of a sample in accordance with embodiments of the present disclosure.

FIG. 31 depicts a software-based graphical user interface for setting a target temperature for a test during testing of a sample in accordance with embodiments of the present disclosure.

FIG. 32 depicts a software-based graphical user interface for setting up a timed test during testing of a sample in accordance with embodiments of the present disclosure.

DETAILED DESCRIPTION

Figure 1:
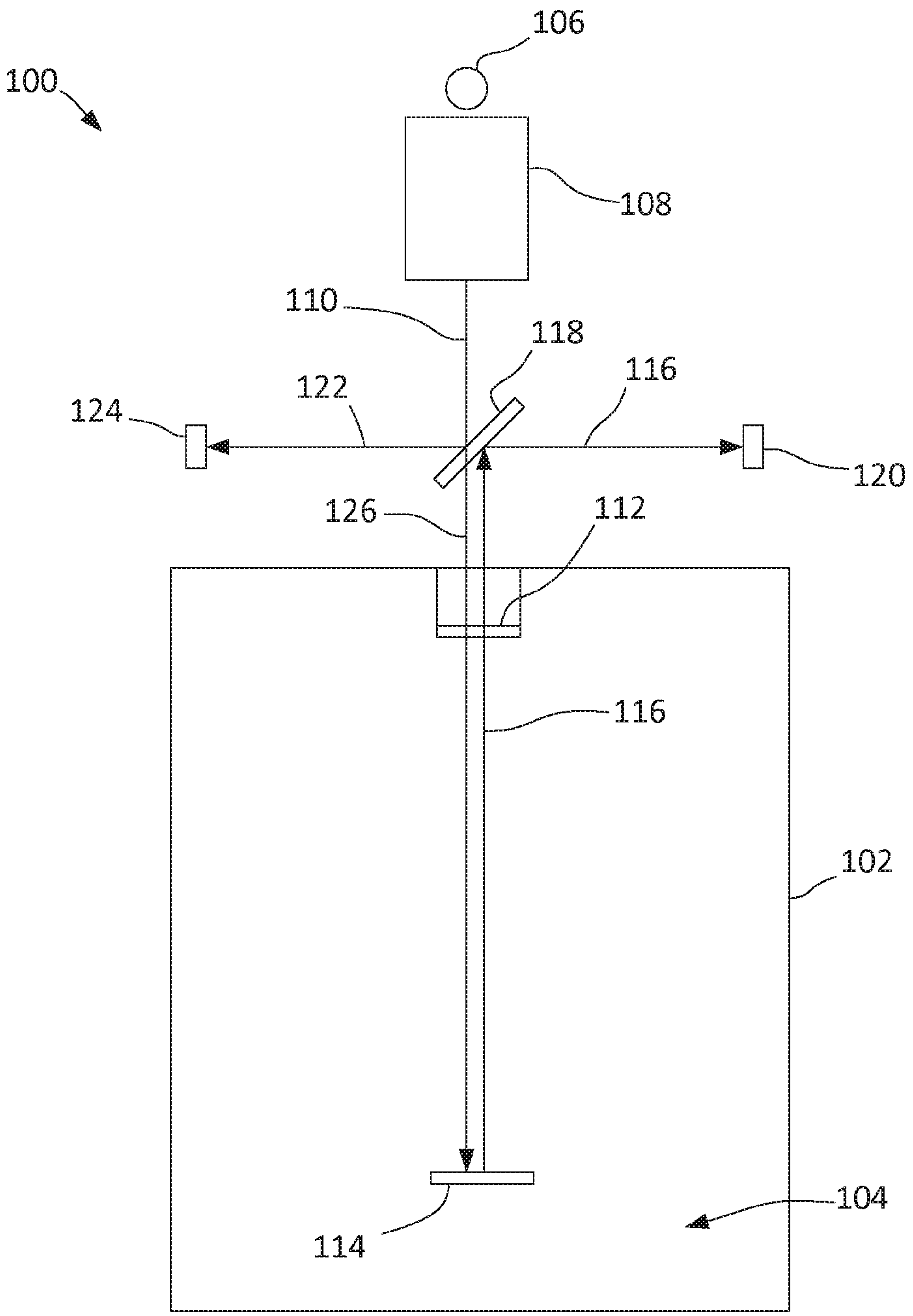
FIG. 1 depicts a system for measuring optical properties of liquid samples with a probe inserted into a liquid sample in accordance with embodiments of the present disclosure.

The present disclosure includes methods, systems, and apparatus for measuring optical properties and, more particularly, measuring the optical properties of a liquid sample within a target environment. As used herein, a "target environment" is an environment in which a liquid sample is present. A target environment may be part of larger environment. In some embodiments, the probe in accordance with the present disclosure is configured to receive and/or isolate a target liquid sample within a target environment. For example, typically a liquid sample is taken from a bulk source of the liquid and is then placed into a measurement device. Embodiments of the present probe-based system are, instead, placed into the bulk source of the liquid. That is, the probe-based system disclosed herein is positioned within the target environment such that the optical properties of the liquid are measured within the target environment, rather than the liquid being transported to a remote location (e.g., a laboratory) for testing. Testing the liquid within the target environment avoids, or at least reduces, errors and disturbances that can occur to a sample during transport (e.g., contamination and temperature changes). When the probe of the probe-based system is inserted into the bulk source of liquid, the probe is within the target environment of the liquid and is surrounded by the liquid, with at least a portion of the liquid entering into a sample inlet of the probe for testing.

The present disclosure includes systems and methods for analyzing liquids. Embodiments include a probe-based, parallel-light spectroscopy system that is configured to perform measurements pursuant to one or more measurement standards. For example, and without limitation, embodiments of the system are configured to perform measurements in accordance with one or more American Society for Testing and Materials (ASTM) standards, Saybolt test standards, Cobalt color test routines, and other standards for measuring haze in liquid samples. In some embodiments, the system is or includes a handheld probe (i.e., a probe that can be operated by hand).

Embodiments of the system include a probe that is configured for in-situ measurements of liquid samples in a target environment (e.g., at the point at which the sample is drawn into a sample container without having to bring a sample to a laboratory or other location). The ability for in-situ measurements facilitates the maintenance of sample integrity; avoiding transportation-related issues including time or temperature impacts on the sample. The probe can include an integrated precision thermocouple that records the temperature at which haze and color testing are performed by the probe. Embodiments of the probe reduce or even eliminate moving parts, such as cuvette sample chamber lids and cooling fans, resulting in a robust system that is less susceptible to mechanical and other failures in comparison to systems with moving parts.

Embodiments of the probe-based system eliminate the need for glass or other sample material cuvettes, which require thorough cleaning and drying, both of which are difficult in some environments. The probe-based system can be cleaned, such as by wiping the surface of the probe (e.g., with a lint-free material and Isopropyl Alcohol).

Rather than using a full-sized spectrophotometer and scattering optics, embodiments of the probe include a compact micro-laser-based spectrophotometer that includes a micro-Peltier Cooling chip and heat sink, which provides for temperature control of the spectrophotometer, minimizes noise, and reduces the variability of results.

Liquid Samples

The liquid samples measured in accordance with embodiments of the present disclosure include, but are not limited to, petroleum-based liquid samples such as petroleum-based fuels or and petroleum-based lubricants. The petroleum-based liquid may be a liquid middle distillate fuel, such as one blended with synthesized hydrocarbons or biofuels. Liquid middle distillate fuels include refinery products in the middle distillation range of refined products, including fuels having from approximately eleven (11) to approximately eighteen (18) carbons present in each molecule thereof. Liquid middle distillate fuels include heating oil, distillate fuel oil, gas oil, lighting oil, and cooking oil. More particular examples of liquid middle distillate fuels include kerosene, jet fuel, diesel fuel, and marine bunker fuel.

Measurement of the optical properties of the liquid samples can be used to determine if the liquid meets one or more optical standards and specifications to confirm quality and lack of water and/or particulates within the liquids. The liquids can be analyzed to determine the presence and amount of contaminate therein. The contaminate can include particulates in the liquid (e.g., particulates in suspension within the liquid), water, or both.

Exemplary Measurement Standards

The optical measurements of the liquid samples can be performed to determine haze, clarity, and/or color of the liquid sample, which can, in-turn, be used to determine the presence and amount (or absence) of contaminate in the liquid. The optical measurements of the liquid samples can be performed in accordance with one or more measurement standards. As would be understood by one skilled in the art, "transmission" through a liquid sample refers to the amount of light that passes through the liquid sample without being scattered; "haze" refers to the amount of light that is subject to wide angle scattering (e.g., at an angle greater than 2.5° from normal (ASTM D1003)); and "clarity" refers to the amount of light that is subject to narrow area scattering (e.g., at an angle less than 2.5° from normal). The "haze" can be measured in accordance with: ASTM D8148 (e.g., ASTM D8148-22), Standard Test Method for Spectroscopic Determination of Haze in Fuels. The liquid samples can be analyzed using spectroscopy to determine the level of suspended water and particulate contamination present therein. Such testing results in the determination of an ordinal, whole-number, Instrument Haze Rating (IHR) of from 1 to 6 and a Haze Clarity Index (HCl) of from 50.0 to 100.0 for a test specimen that is at a specified temperature or range, such as 22.0° C.±2.0° C. As used herein, the "HCl" is a numerical value of from 50.0 to 100.0 that indicates fuel clarity derived from spectroscopic measurements and an algorithm that processes the spectroscopic measurements. The HCl values increase with sample clarity and range from 100.0 HCl for a relatively clear and bright sample to 50.0 HCl for a relatively cloudy and opaque sample. For example, a fuel with an HCl value of 90 has less haze than a fuel with an HCl value of 80. HCl can be used to evaluate haze intensity changes within a given IHR. In accordance with ASTM D4175, Haze Clarity Index (HCl) is an empirical definition of the haze of a middle distillate fuel based on a scale of 50 to 100 as determined by ASTM Test Method D8148. In accordance with ASTM D4176, Haze Clarity Index (HCl) is an empirical definition used to estimate the presence of suspended free water and solid particulate contamination in distillate fuels by generating a numerical value from 50.0 to 100.0 as determined by Test Method D8148. As used herein, the IHR is an ordinal, whole number of from 1 to 6 that corresponds to haze ratings defined in ASTM Test Method D4176—Procedure 2, and is assigned to a test specimen based upon spectroscopic measurements and an algorithm that processes the spectroscopic measurements.

The determination of the color of petroleum products may be used for manufacturing control purposes and provides an indication of the quality characteristics of the liquid, as color is readily observed by the user of the product. In some cases, color may serve as an indication of the degree of refinement of the material. In some aspects, "color", as used herein, is measured in accordance with any of the following standards: ASTM D156-15, Standard Test Method for Saybolt Color of Petroleum Products (Saybolt Chromometer Method); ASTM D1500-12 (2017), Standard Test Method for ASTM Color of Petroleum Products (ASTM Color Scale); ASTM D6045-12 (2017), Standard Test Method for Color of Petroleum Products by the Automatic Tristimulus Method; ASTM D5386-16, Standard Test Method for Color of Liquids using Tristimulus Colorimetry; and ASTM D1209-05 (2011), Standard Test Method for Color of Clear Liquids (Platinum-Cobalt Scale).

System Components

With references to FIGS. 1-5, embodiments of a parallel-light spectroscopy system for measuring the optical properties of liquid samples is depicted. System 100 includes a sample chamber 102 for receipt of a liquid sample 104 through a sample inlet (not shown).

A multi-wavelength light source 106 is positioned and configured to direct multi-wavelength light into the liquid sample 104. In some embodiments, the light source 106 is a high-intensity, small-spot light source.

Figure 2:
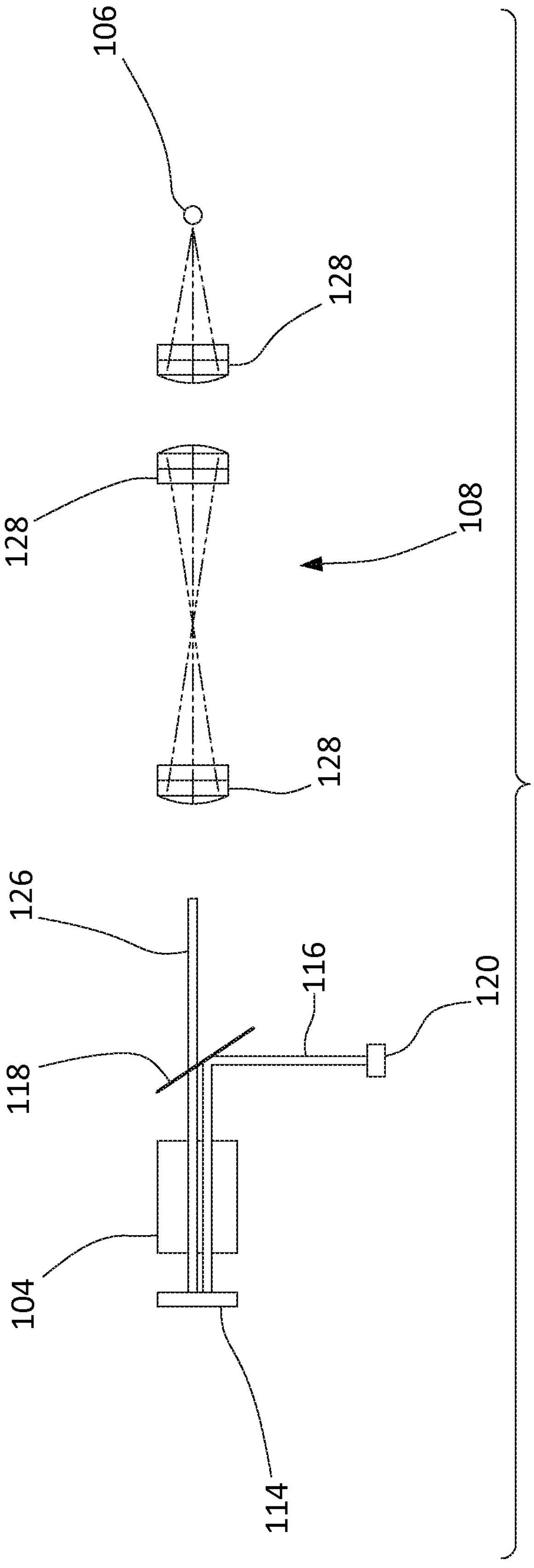
FIG. 2 depicts a system, in accordance with embodiments of the present disclosure, including components of the system that interact with light.
Figure 3:
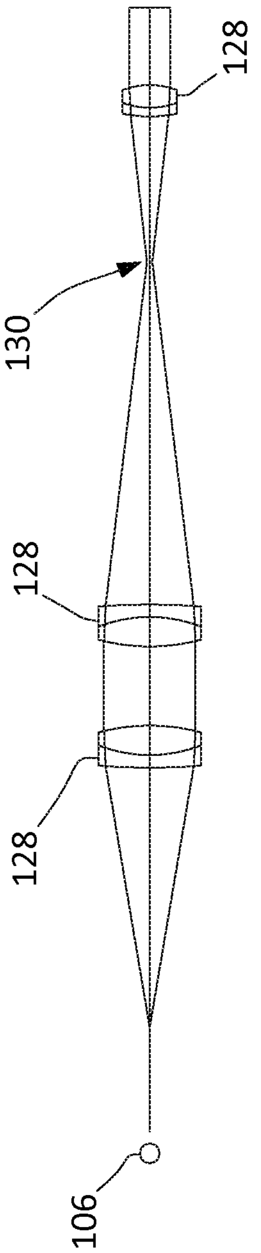
FIG. 3 depicts a collimator, in accordance with embodiments of the present disclosure, showing the interaction between the collimator and light.

A collimating optical chain, collimator 108, is positioned between the light source 106 and the liquid sample 104 for narrowing a beam of light 110 emitted from the light source 106 prior to the beam of light 110 passing though the liquid sample 104. In some embodiments, the collimator 108 includes one or more achromatic doublet lenses 128 and a pinhole 130, as shown in FIGS. 2 and 3.

Light 110 passes from collimator 108 to beamsplitter 118. Beamsplitter 118 directs (e.g., reflects) a portion of light 110, first portion of light 122, to a first light sensor 124 for measurement of an intensity of the light 110 emitted from the light source 106.

The beamsplitter 118 directs the remainder of the light 110, second portion of light 126, through window lens 112 and through the liquid sample 104 within the sample chamber 102. After passing through the liquid sample 104, the second portion of light 126 impacts with a return mirror 114 that is positioned within the sample chamber 102. The return mirror 114 reflects return light 116 back towards the beamsplitter 118. The beamsplitter 118 then directs the return light 116 to a second light sensor 120. The second light sensor 120 measures the intensity of the return light 116 that has passed through the liquid sample 104.

The measurements of intensity taken by the first sensor 124 and the second sensor 120 can be compared, as a function of wavelength, to determine the light-absorbing intensity of the liquid sample 104. The light-absorbing intensity of the liquid sample 104 can then be correlated to an amount of contaminant in the liquid sample 104. The results of the measurements by the first sensor 124 and second sensor 120 can be digitally translated to determine specific optical properties. One or both of the sensors 120 and 124 can be or include a multi-wavelength light sensor having integrated channels for XYZ and NIR measurements. The system 100 can be configured with one or more mirrors or other reflective objects (e.g., mirror 114) to direct light to the desired location(s) and/or imaging lenses or other focusing objects (e.g., lens 112).

Figure 4:
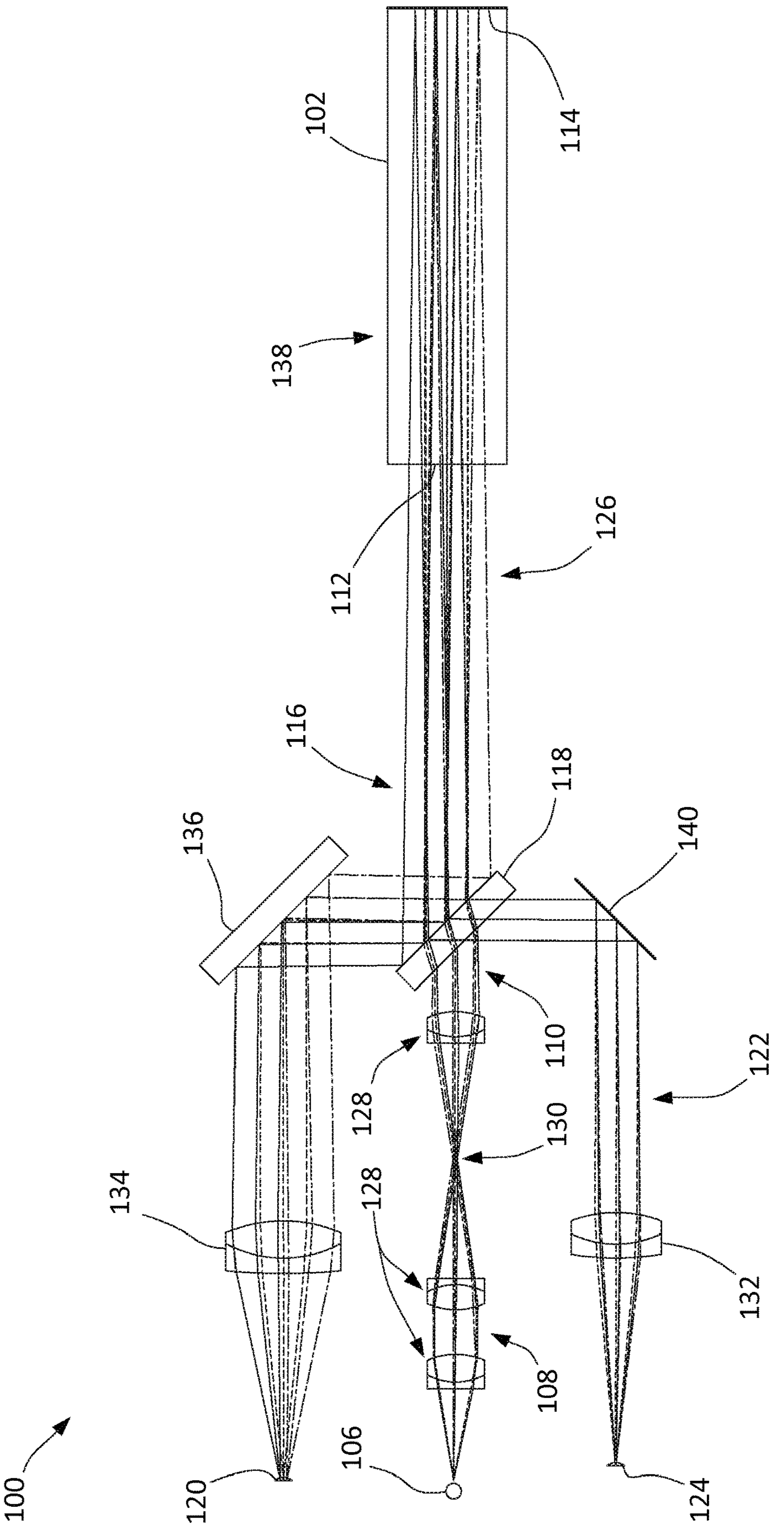
FIG. 4 depicts a system, in accordance with embodiments of the present disclosure, showing the pathways of light travel in the system.
Figure 5:
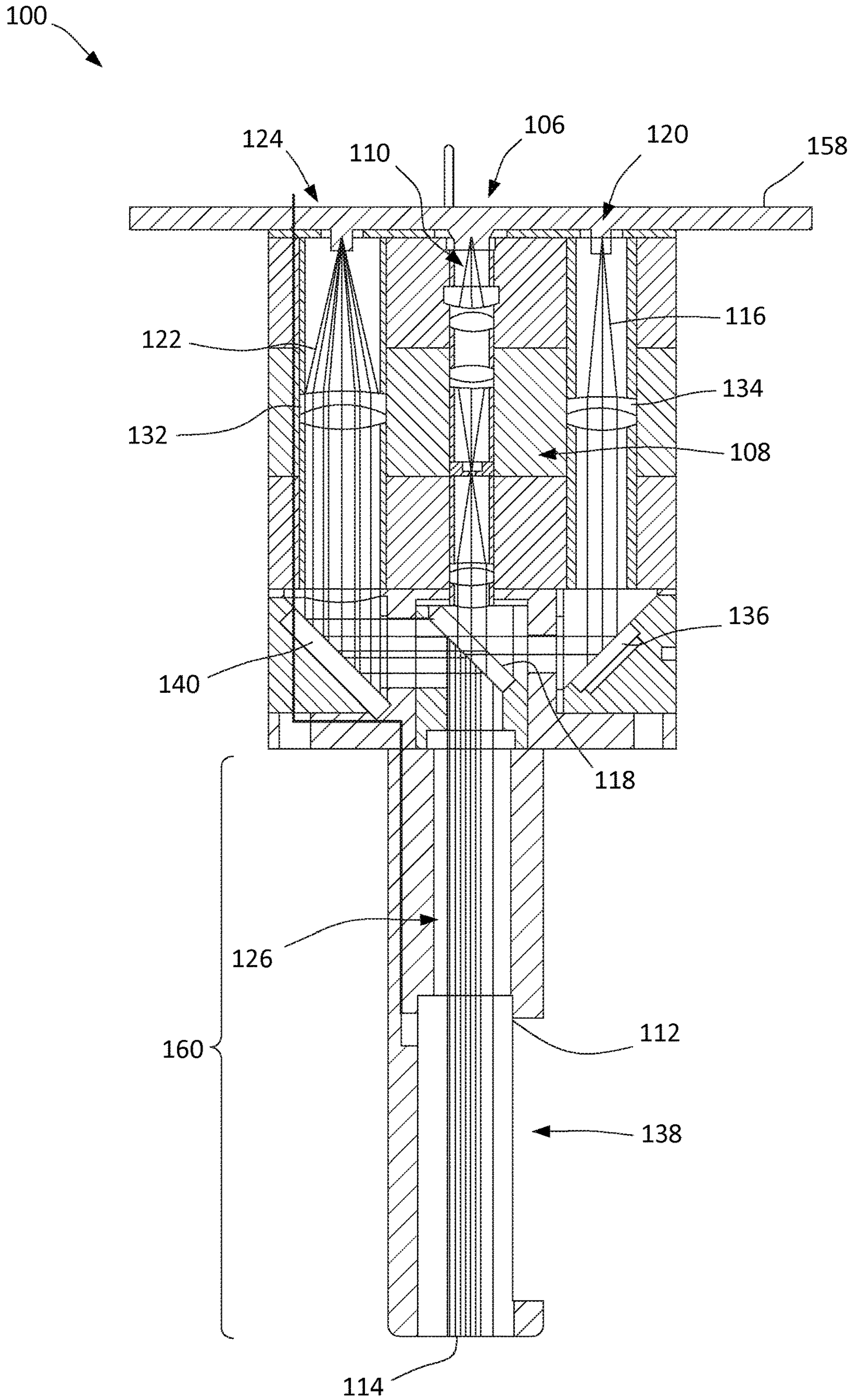
FIG. 5 is a cross-sectional view of a system, in accordance with embodiments of the present disclosure, showing internal components of the system and light pathways in the system.

With reference to FIG. 4, system 100 includes a sample inlet 138. When the sample inlet 138 is positioned within a liquid sample, at least a portion of the liquid enters (e.g., flows into) the sample chamber 102 through the sample inlet 138. With the liquid sample in the sample chamber 102, light source 106 directs light 110 through collimator 108. Within collimator 108, the light 110 passes through a series of collimating lenses 128 and pinhole 130. In the embodiment shown in FIG. 4, the light 110 passes through two collimating lenses 128, then the pinhole 130, and then a third collimating lens 128.

After passing through the collimator 108, the light 110 is directed to the beamsplitter 118. The beamsplitter 118 splits the light 110 into two portions, including light 122 and light 126. Beamsplitter 118 directs light 122 to a folding mirror 140. Folding mirror 140 directs light 122 to an imaging lens 132. Imaging lens 132 directs light 122 to first sensor 124 for measurement thereof.

The beamsplitter 118 directs light 126 through a sample chamber window lens 112 and into the sample chamber 102 for interaction with the liquid sample therein. After passing through the liquid sample within the sample chamber 102, the light 126 impacts the return mirror 114. The return mirror 114 reflects the light, as return light 116, back through the window lens 112 and to the beamsplitter 118 as return light 116. The beamsplitter 118 directs the return light 116 to folding mirror 136. The folding mirror 136 directs the return light to imaging lens 134. The imaging lens 134 directs the return light 116 to second sensor 120 for measurement thereof. In some embodiments, the light 126 and the return light 116 travel along parallel, but directionally opposite, pathways for at least a distances (e.g., between the beamsplitter 118 and the return mirror 114).

Figure 6:
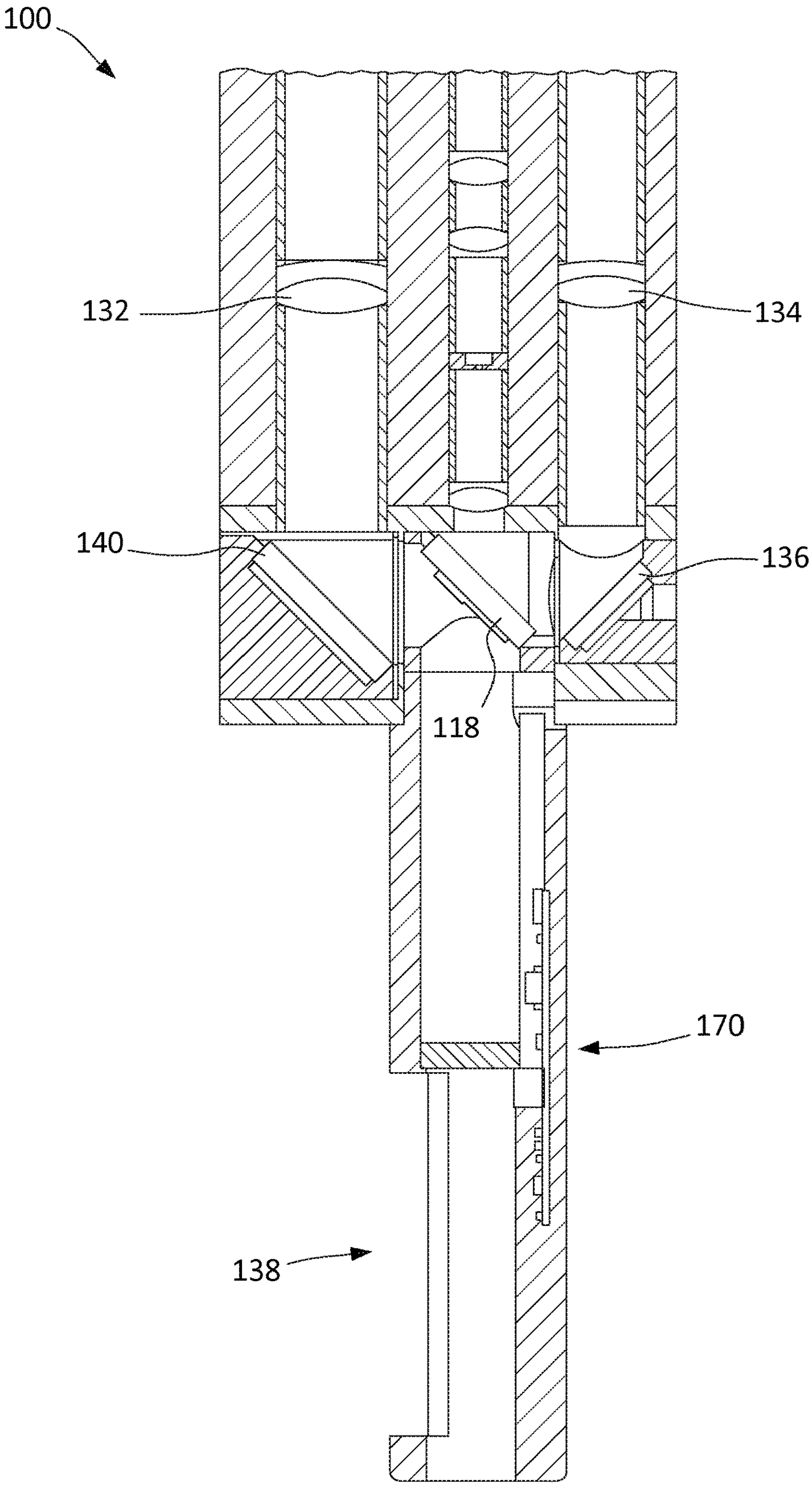
FIG. 6 is a cross-sectional view of a system, in accordance with embodiments of the present disclosure, showing internal components of the system including a temperature sensor and scatter sensor.

With reference to FIG. 6, in some embodiments, the system 100 includes a sensor package 170 positioned within the probe 160 (e.g., within or adjacent the sample inlet 138). The sensor packet 170 can include a detector for measuring light scatter (i.e., portions of light 126 that is scattered as a result of passing through a liquid sample). The sensor package 170 includes a circuit and microsensor for measuring the temperature of liquid samples. For example, the haze can be tested at certain temperatures via use of the temperature sensor 170. The system 100 can be programmed to test haze when the sample reaches a preset temperature or is within the a preset temperature range.

Figure 7:
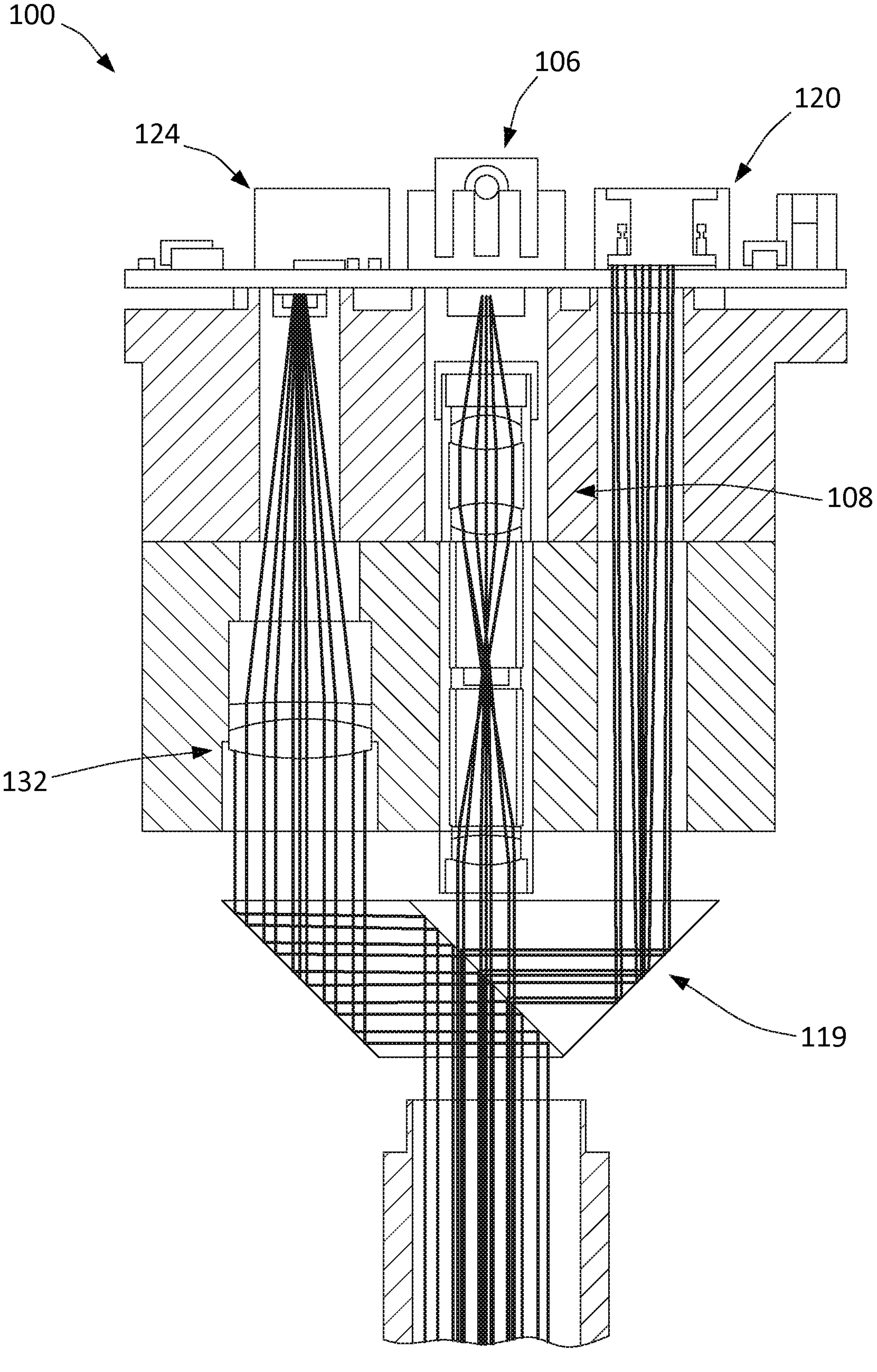
FIG. 7 depicts a cross-section of a portion of a system, in accordance with embodiments of the present disclosure, with a beam-splitter and mirrors.

In some embodiments, the system 100 includes a beamsplitter and mirror unit 119 that combines the functions of the beamsplitter 118 with the folding mirrors 136 and 140 into a single piece to increase stability of the system 100, as shown in FIG. 7.

One skilled in the art would appreciate that the system disclosed herein is not limited to the particular arrangement and number of lenses, mirrors, and other components, as shown in FIGS. 1-7.

Sensor

Figure 8B:
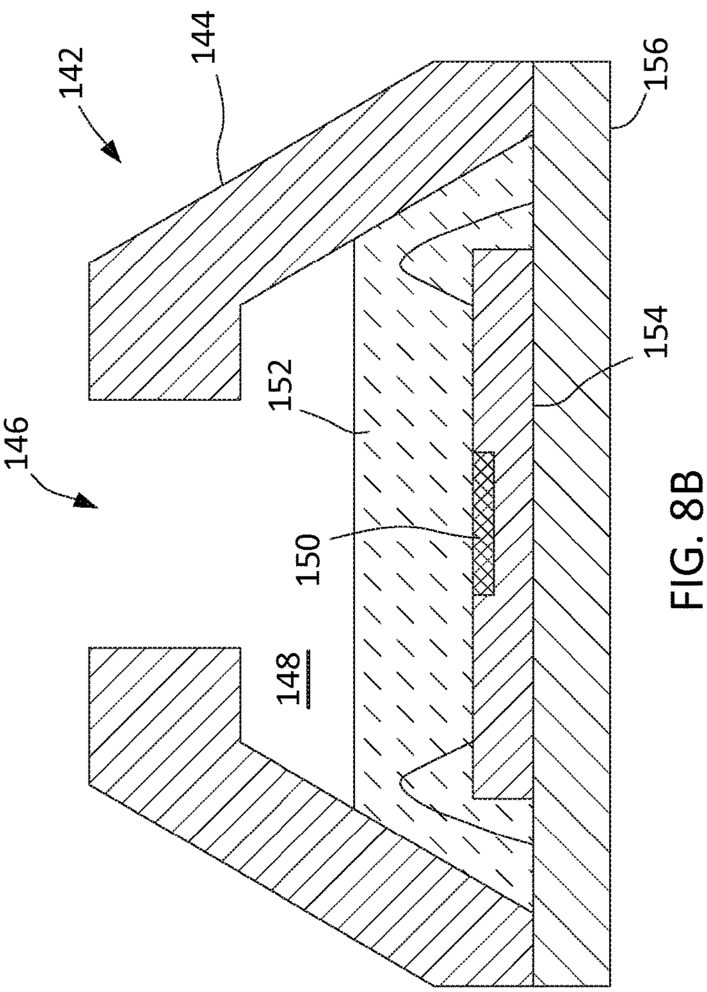
FIG. 8B is a cross-sectional view of the light sensor in accordance with embodiments of the present disclosure.
Figure 8A:
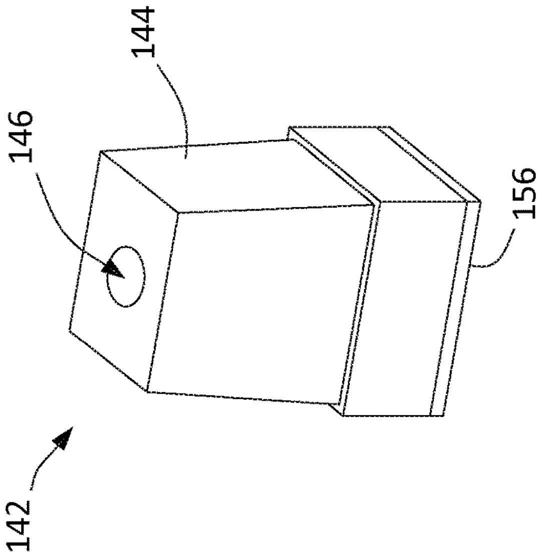
FIG. 8A depicts a light sensor in accordance with embodiments of the present disclosure.

FIGS. 8A and 8B depict an embodiment of a sensor package or portion thereof. Sensor package 142 may be the same or similar to the sensors 120 and 124. Sensor package 142 includes body 144. The body 144 includes or defines an inlet 146, which provides for receipt of light and passage of the light into a chamber 148 of the sensor package 142. Within the chamber 148, the sensor package 142 includes one or more sensors 150. The sensors 150 are positioned within a clear epoxy 152 and supported on a die 154 and substrate 156.

Figure 9:
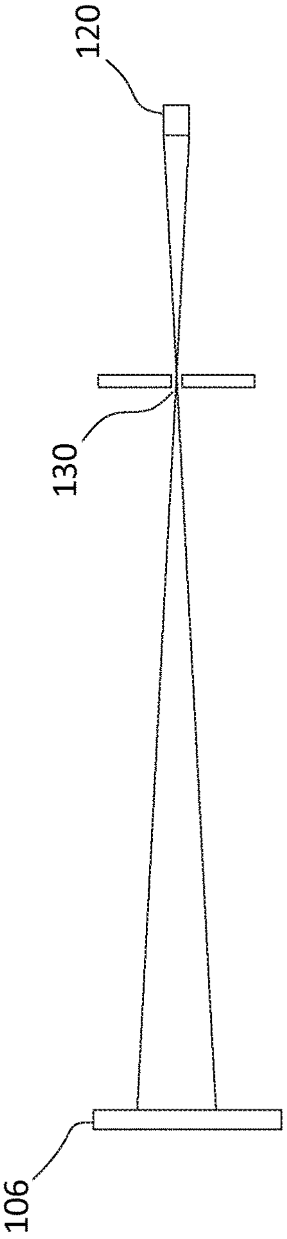
FIG. 9 is a schematic of a light source, pinhole, and detector in accordance with embodiments of the present disclosure.

In one exemplary embodiment, the sensors disclosed herein include a 1 $mm^2$ area detection area and is optimized for diffused light. Using a pinhole camera to image the diffused light source at the sensor can eliminate the stray light from other sources, such as ambient, and other surfaces, such as the walls of the liquid container. The pinhole diameter can be designed to optimize the signal-to-noise selection. The distance can be designed to manage the image size at the detector to select the ROI of the light source. FIG. 9 depicts a simplified schematic of a light source 106, pinhole 130, and detector 120 in accordance with embodiments of the disclosure.

Figure 10:
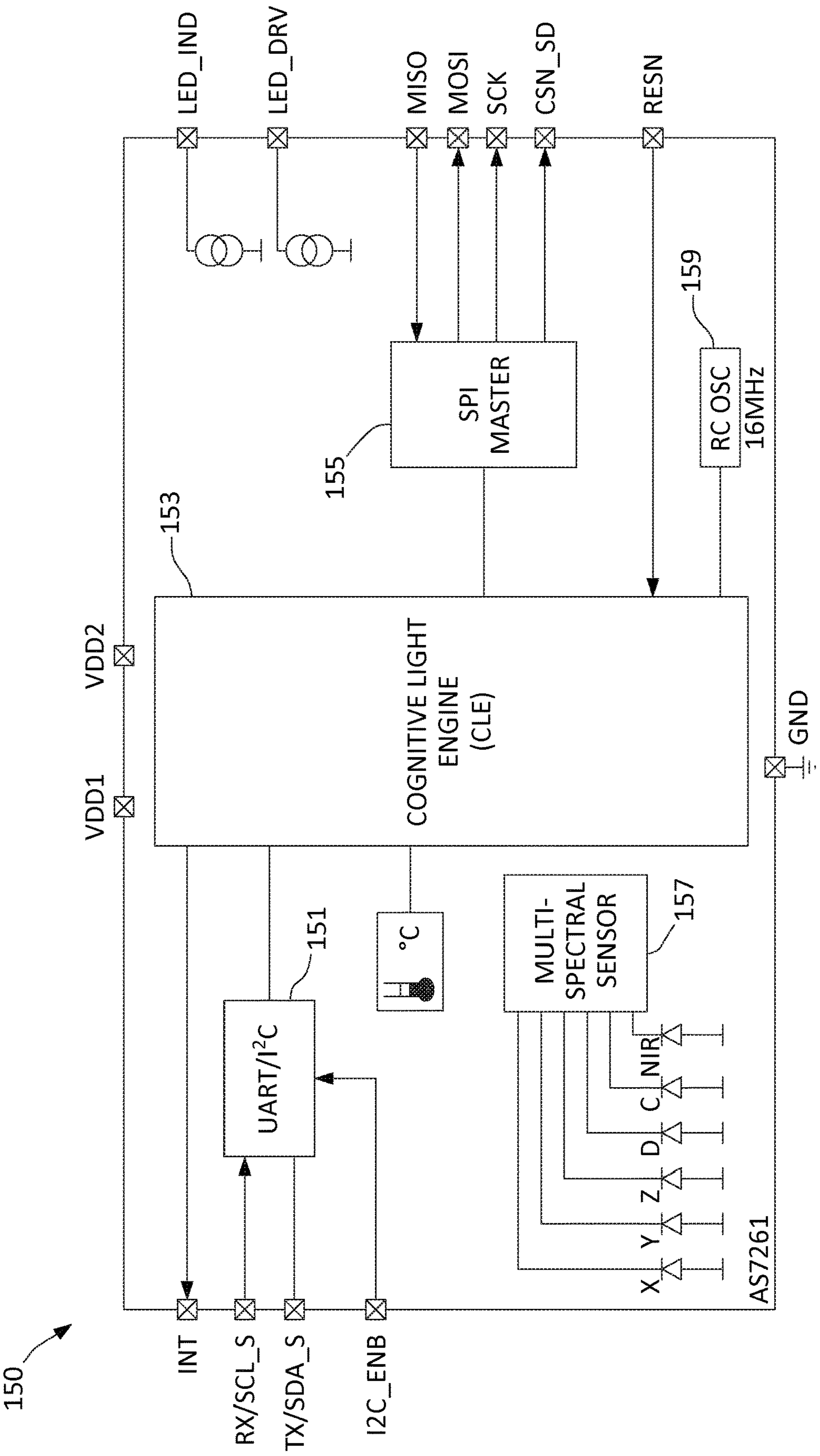
FIG. 10 depicts components of a light sensor in accordance with embodiments of the present disclosure.
Figure 12:
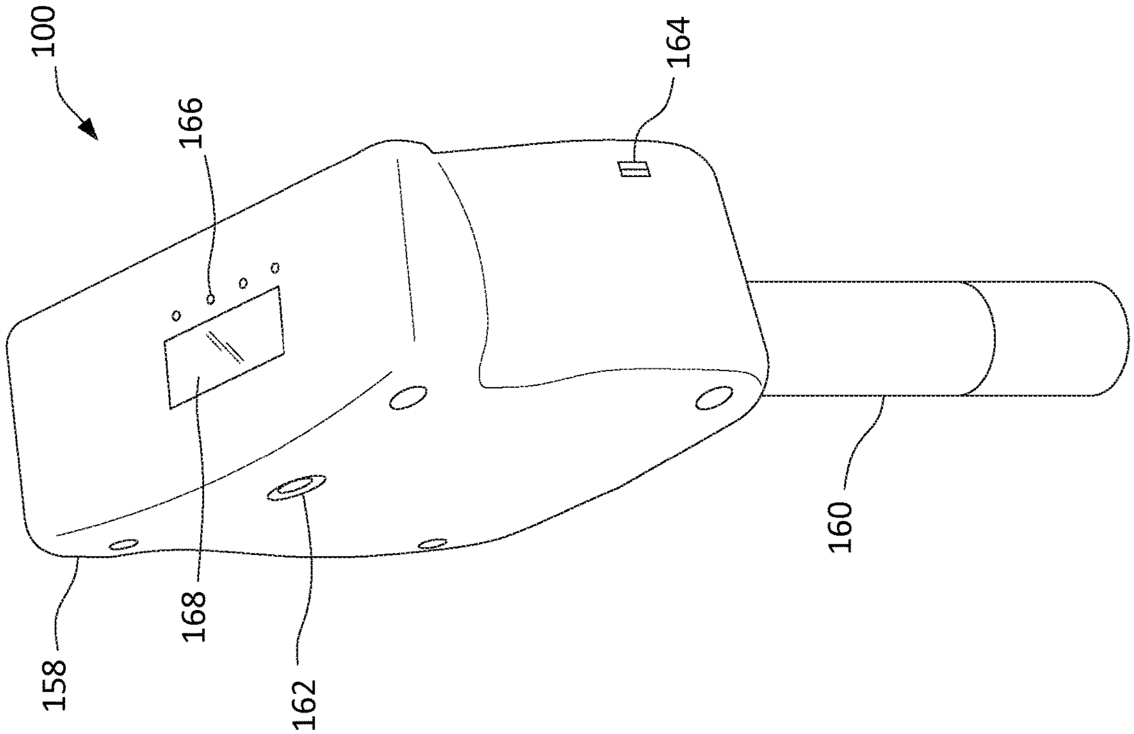
FIG. 12 is another perspective view of a system in accordance with embodiments of the present disclosure.
Figure 11:
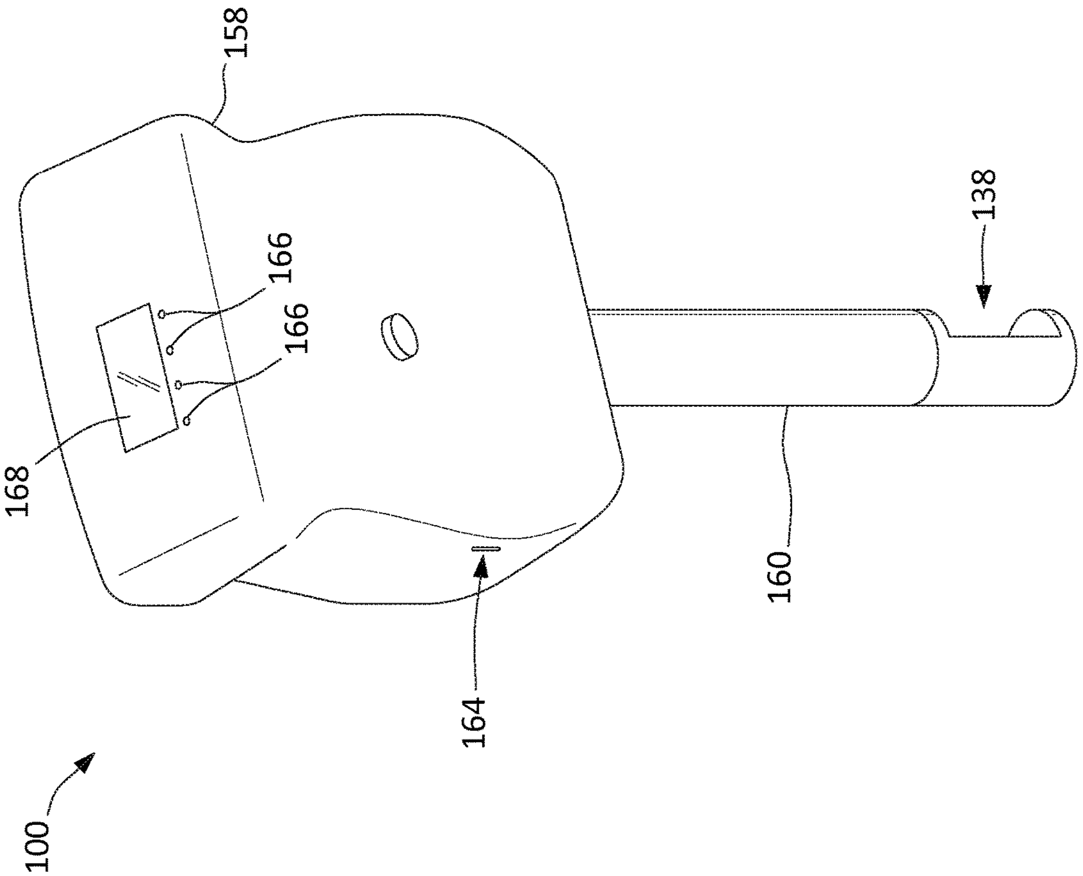
FIG. 11 is a perspective view of a system in accordance with embodiments of the present disclosure.
Figure 14:
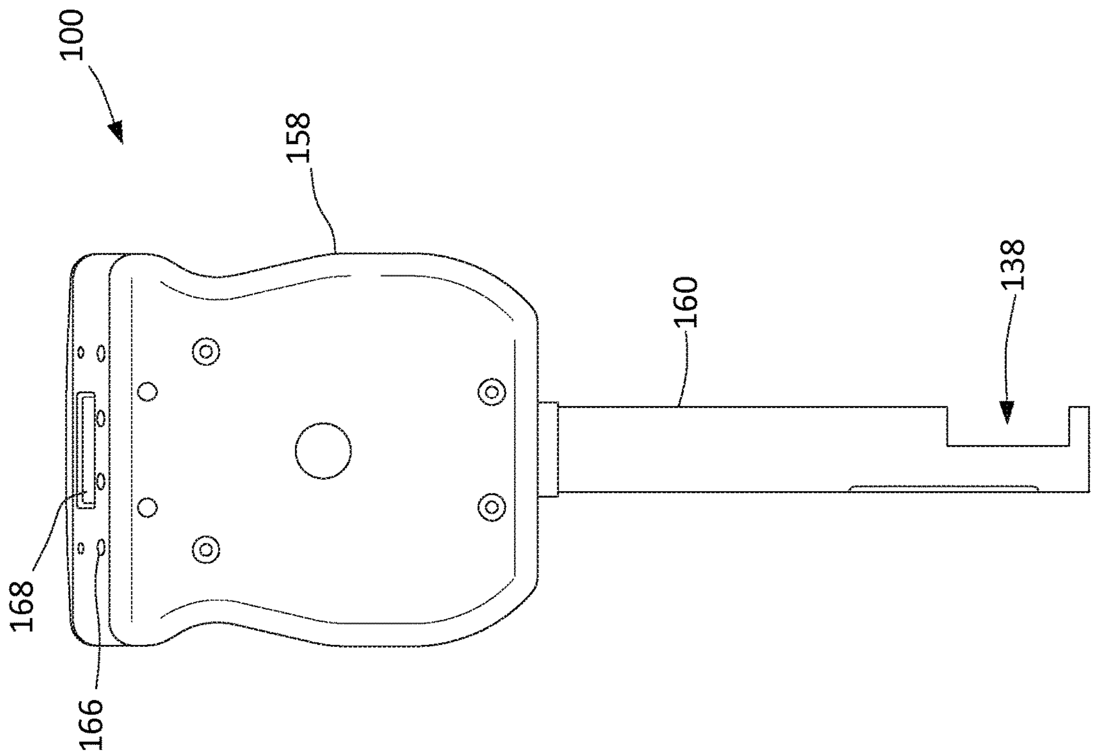
FIG. 14 is a back view of a system in accordance with embodiments of the present disclosure.
Figure 13:
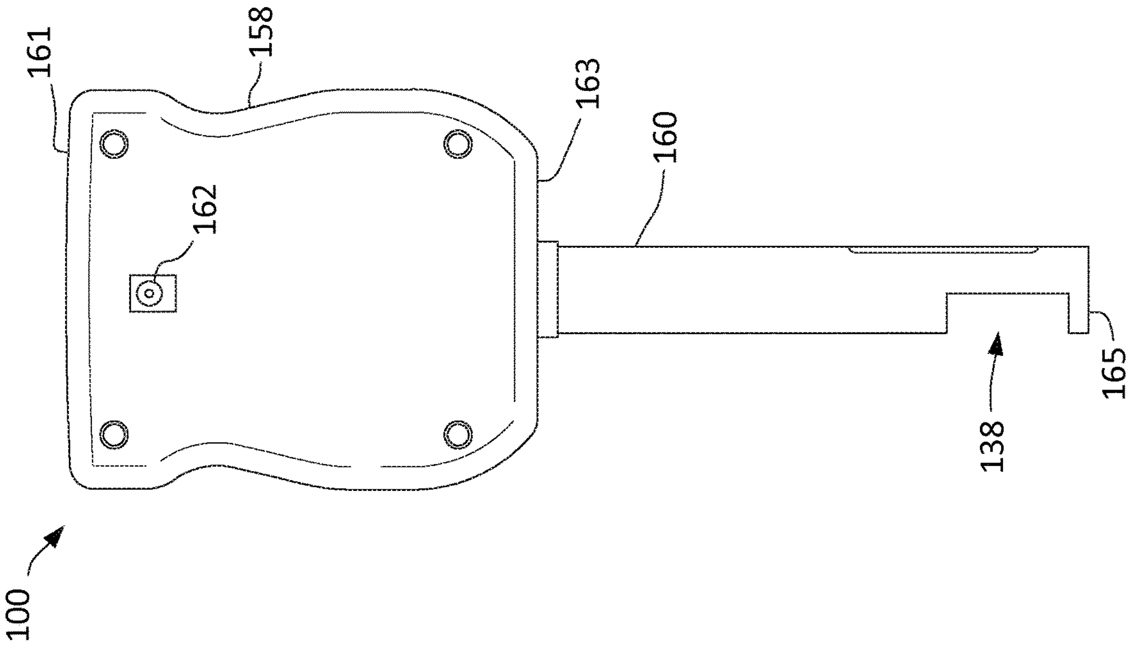
FIG. 13 is a front view of a system in accordance with embodiments of the present disclosure.
Figure 16:
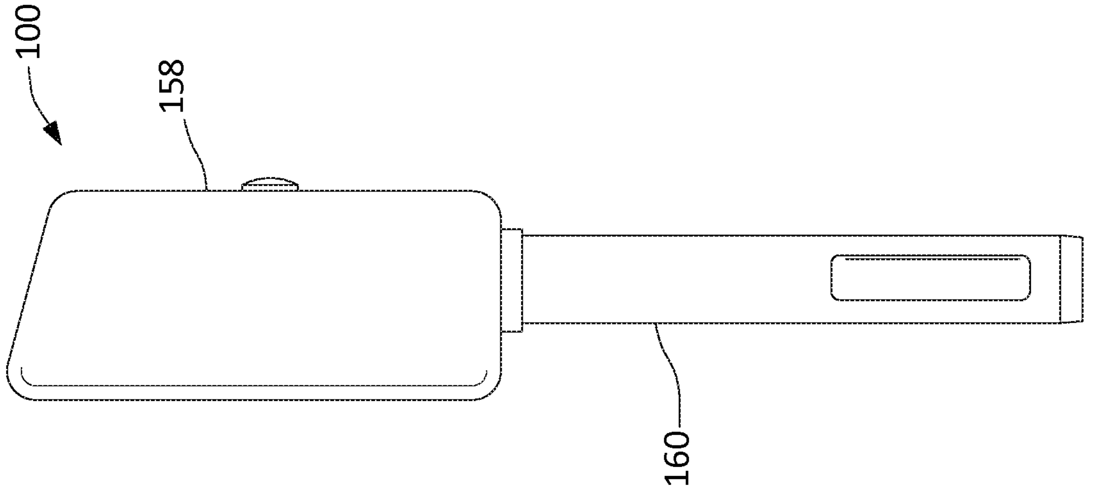
FIG. 16 is a second side view of a system in accordance with embodiments of the present disclosure.
Figure 15:
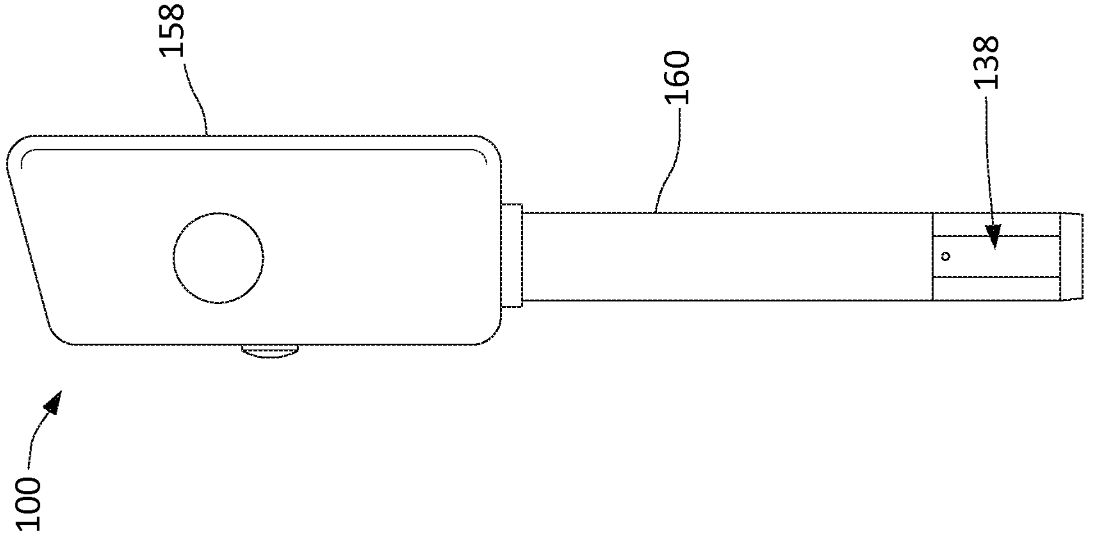
FIG. 15 is a first side view of a system in accordance with embodiments of the present disclosure.
Figure 17:
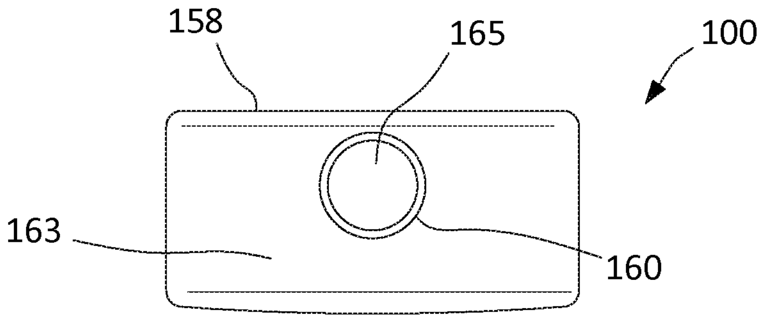
FIG. 17 is a bottom view of a system in accordance with embodiments of the present disclosure.
Figure 18:
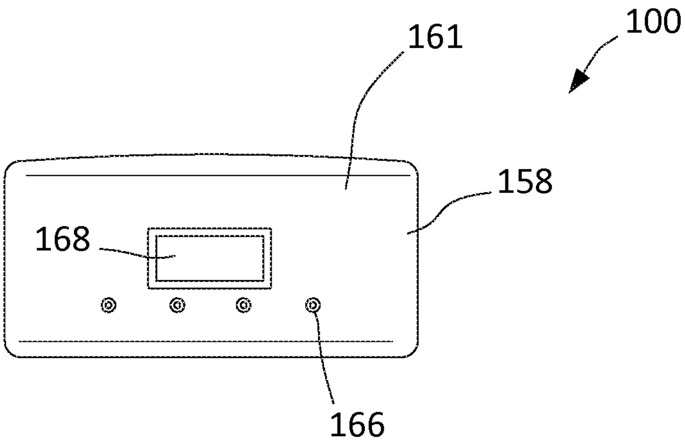
FIG. 18 is a bottom view of a system in accordance with embodiments of the present disclosure.

FIG. 10 depicts components of an exemplary sensor 150. Sensor 150 includes a universal asynchronous receiver-transmitter 151, a cognitive light engine 153, serial peripheral interphase 155, a multispectral sensor 157, and an RC oscillator 159.

One skilled in the art would appreciate that the sensors disclosed herein are not limited to the particular embodiment as shown in FIGS. 8A-10.

Probe

In some embodiments, the system disclosed herein is in the form of a probe. With reference to FIGS. 11-18, exemplary embodiments of the system in the form of a probe are depicted. One or more components of the system 100 can be contained within a housing 158. The housing 158 contains the sensors; lenses; mirrors; beamsplitter; light source; collimator; computer hardware, and other components of the system 100. An elongated probe 160 extends from the housing 158. The elongated probe 160 is configured to be inserted into a liquid sample, while allowing the remainder of the housing 158 to remain outside of the liquid sample. The probe 160 contains or includes the window lens, sample inlet 138, return mirror, and sensor package (for measuring scatter and temperature).

The housing 158 includes a power butter 162 for turning the system 100 on an off, a USB port 164 for charging the system 100 and/or for transmitting data to and from the system 100, control buttons 166 (here shown as four control buttons) for controlling the functions of the system 100, and an OLED display 168 for displaying data, prompts, and other information. In some embodiments, the OLED display 168 and control buttons 166 are on a top surface 161 of the body 158, the probe 160 extends from a bottom surface 163 of the body 158, and the sample inlet 138 is positioned along the probe 160 between the bottom surface 163 of the body 158 and a bottom surface 165 of the probe 160. The sample inlet 138 can be a void space in the probe 160 that is in optical communication with the light source 106 such that light can pass through the void of the sample inlet 138 and any liquid therein.

Figure 20:
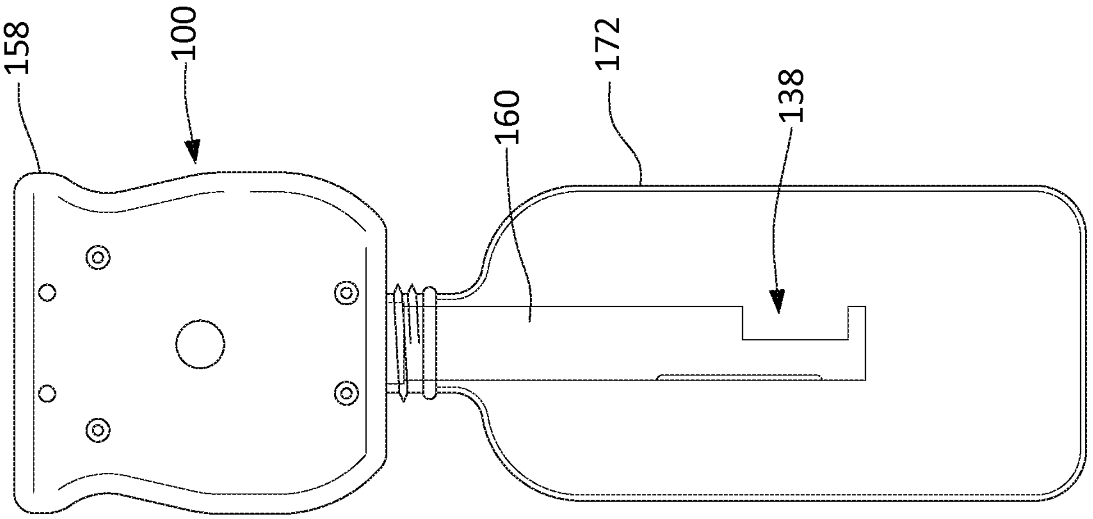
FIG. 20 depicts a probe inserted into a sample bottle in accordance with embodiments of the present disclosure.
Figure 19:
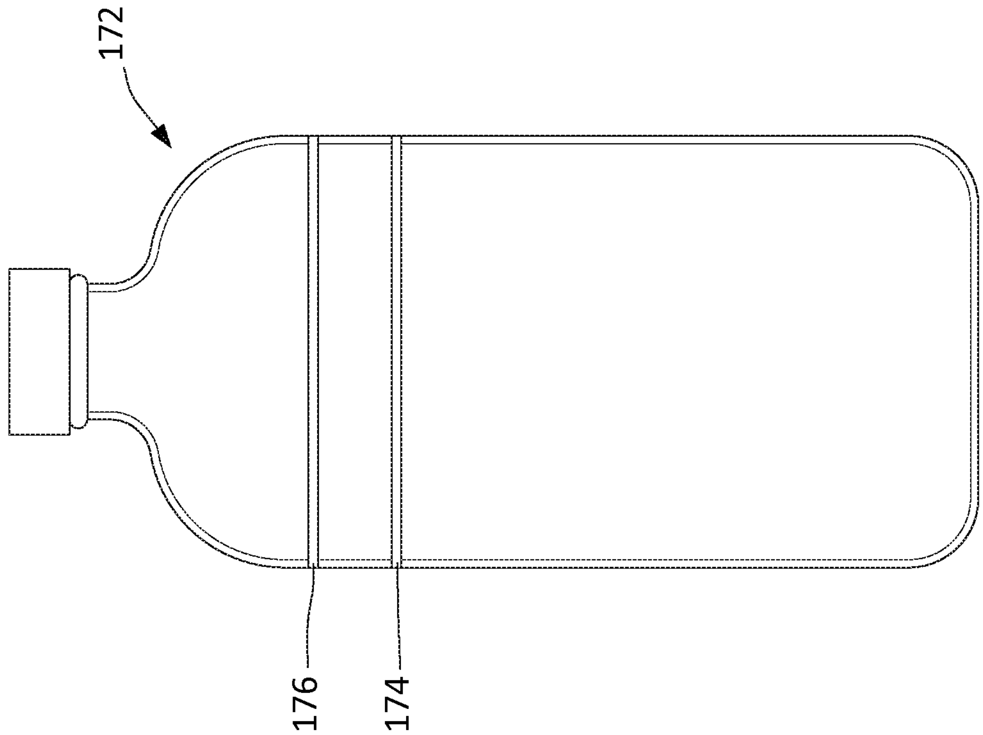
FIG. 19 depicts an exemplary sample bottle in accordance with embodiments of the present disclosure.

The handheld probe embodiment of the system 100 is configured to be used with fuel industry-standard bottles, such as bottle 172 shown in FIGS. 19 and 20. FIG. 19 depicts an exemplary container 172 in which a liquid sample can be measured using the probe disclosed herein. The container 172 has a minimum fill line 174 and maximum fill line 176. As shown in FIG. 20, the probe 160 of the system 100 is inserted into the bottle 172 until the probe 160 is at least partially surrounded by a liquid sample (not shown) and at least a portion of the liquid enters into the sample chamber through the sample inlet 138. Other portions of the system 100, such as the housing 158 with the light source 106, are maintained outside of the container 172 and outside of the liquid sample. Thus, the system 100 is configured such that active components of the system 100 within the housing 158 (e.g., the light source 106 and sensors 120, 124) are maintained out of the liquid sample, while allowing complete immersion of the sample inlet 138 on the probe 160 into the container 172. The sample inlet 138 has a length that is sufficient such that the container 172 can be filled only partially with the entire sample inlet 138 being submerged within the liquid sample 171. The handheld probe can be placed and rested on the container 172 during the testing. Using an industry-standard bottle as the container 172 increases the volume of the sample liquid tested and decreases the effects of contaminants compared to testing methods that require use of small sample sizes. The handheld probe can be Bluetooth-enabled and include USB port 164 for charging and data transmission.

Method of Measuring Optical Properties

Embodiments of the present disclosure include methods of measuring optical properties of liquids. The method of testing a liquid sample can include inserting the probe of the system into a container that contains a liquid sample. For example, the liquid sample can be drawn into the container at a pipeline using a sample spigot and letting gravity fill a jar or other type of container. The probe of the system is lowered into the container and inserted into the liquid sample within the container for testing. When the probe is inserted into the liquid sample, a portion of the liquid sample passes into the sample chamber of the probe through the sample inlet. The sample inlet can be precisely designed to maximize required path link between the NIR light and scattering light source and the optical detectors that record the amount of light received or detected. With the probe in the liquid sample, the light source provides light to the optical-lens chain, collimator, to collimate the light from the light source. The beamsplitter then splits the collimated light into reflective light and transmitted light. The reflected light passes to a first light sensor that measures the intensity of the reflective light emitted from the light source. The transmitted light is directed through the liquid sample and is reflected from a return mirror back to the beamsplitter which directs the transmitted light through an imaging lens to a second sensor. The second sensor the measures the intensity of the transmitted light. In some embodiments, instead of being reflected by a return mirror, the transmitted light is directed to a second sensor that is located at an end of the sample inlet. The second sensor detects the intensity, as a function of wavelength, of the light transmitted through the controlled length of the liquid sample. By comparing the intensity of the reflected light and the intensity of the transmitted light, the light-absorbing intensity of the liquid sample is determined. These results can be digitally translated to measure specific optical properties. The data from the sensors can be transmitted to a CPU located in the probe (or external). The CPU computes values received by the sensors into measurements that are used in the industry, such as Haze Clarity Index (HCl), Instrument Haze Rating (IHR) and Saybolt, ASTM and Platinum Cobalt APHA color scales. For example, computer instructions stored in a data storage of the system can instruct the CPU to process the sensor data in accordance with one or more such standards.

In operation, the one or more mirrors can be used to direct the light (either or both the reflective light and the transmitted light) throughout the system to, for example, the sensors. Additionally, one or more imaging lenses can be used to intensify either or both the reflective light and the transmitted light before detection by the sensors. In some embodiments, both the reflective light and the transmitted light are directed from the beamsplitter to a folding mirror, and then through imaging lenses before reaching the sensors.

In some embodiments, the system is designed with one or more mirrors optically aligned and attached to the beamsplitter. Combining the beamsplitter and one or more mirrors into a single, assembled piece increases the stability of the system by reducing the alignment dependency between the beamsplitter and the one or more mirrors when comprised of separate pieces. As a single, combined piece, deviations in the rotation or movement of the beamsplitter and mirror piece will have less effect on the operation of the system.

The system is capable of simultaneously measuring haze and color in a sample, such as by using a broad-spectrum, dual laser-excited light source that emits multiple wavelengths, including both white light and NIR, as well as using a single detector with multiple integrated channels for the measurement of color (X, Y, Z) and NIR for haze. The ability to measure the intensity of the light source with every sample test is more efficient than current techniques in the field. The system is not dependent on test-by-test calibration to set standards, which eliminates the need for empty chamber testing in bench-top analyzers; thereby, greatly reducing testing time. The probe can be inserted directly into a sample, which reduces or eliminates inaccuracies caused by light-absorption and/or refractive properties of sample cups. The measurement of the optical properties of a sample determined by comparative testing of the source light and transmitted light for each test reduces or eliminates differences in the intensity of light source. In some embodiments, a thin-film glass plate is used for absolute calibration for both color and haze. Establishing a digital relationship between the source light and transmitted light to measure optical properties of sample liquids is efficient and reliable.

Collimating the light source improves the signal-to-noise ratio and allows for a smaller light source, which is preferable for a hand-held instrument probe. The system is configured to be independent of the refractive index of the testing sample and the sample holder and reduced or eliminates effects of ambient and divergent light. In a preferred embodiment, the collimator includes a broadband achromatic doublet lenes to account for multiple wavelengths.

The multi-wavelength system disclosed herein enables the effective measurement of small-particle-size contaminants in liquid samples, such as water and wax in petroleum fuels, which have different absorption or scattering effects at different wavelengths.

Some exemplary components and aspects of embodiments of the system are set forth in Table 1, below.

TABLE 1

| Component | Features |
|---|---|
| Light source | Sold-state<br>Broad spectrum<br>Small-spot source<br>Dual laser-excited light source with white light and NIR<br>High intensity |
| Pinhole Collimator | Standard 2-stage, 3-lens design<br>Spatial filter to remove off-axis light<br>Broadband achromatic doublet lenses for visible light and NIR |
| Beam splitter | Plate design, cube design, prism design<br>Broadband lens<br>Normalize source variation |
| Sample Calibration | Thin-film coating glass<br>Double-pass |
| Imaging Lens | Increase the intensity/focus of the transmitted light for enhanced output |
| Light Sensor/ Detector | AS7261<br>6 Integrated channels for color (X, Y, Z), NIR (haze), clear (total transmission of light), and dark (elector-noise) measurements<br>16-bit AD converter<br>Smart interface; integrated serial communication |
| Temperature probe | inside of sample inlet for sample temperature at the time of Haze test |
| Scatter sensor | |

Software

The system disclosed herein can be configured to conduct a single test, multiple tests, timed tests, and/or haze at-temperature tests. The color tests can be in accordance with one or more of: ASTM D6045, Saybolt, and ASTM E313 (D5386). The haze test can be in accordance with one or more of: ASTM D8148; HCl correlation to IHR 1-6. The system can include software configured to process the data collected by the sensors and/or to direct the actions of the system. The software can be resident on the probe and/or external of the probe. Results of the tests performed by the system can be depicted graphically and/or as a numerical output. The data from the system can be transferred to other devices, such as a tablet, through Bluetooth and/or the USB port.

FIGS. 21-32 depict some exemplary graphical user interface (GUI) screens of the system for display on the screen 168. Using the GUI 200, a user can select a sample name 299 (FIG. 21). The GUI 200 includes additional controls such as a power button 201 to turn the system on and off, a delete button 203 to delete a selection, a back button 205 to return to the previous screen, a home button 207 to return to a home screen of the GUI 200, and a next button 209 to proceed to the next screen of the GUI 200. After a sample name is selected, the user can hit the next button to proceed to the screen shown in FIG. 22 where the user can then use the GUI 200 to select a test type 297, such as haze test, Saybolt test, ASTM test or Platinum Cobalt test. After a test type is selected, the user can hit the next button to proceed to the screen shown in FIG. 23, where the user can then use the GUI 200 to select a testing method 295, such as single test, multiple test, timed test, or at temperature test (FIG. 23). A single test can include testing a sample one time. Multiple tests can include testing a sample multiple times. A timed test can include testing a sample over a period of time. A temperature test can include testing a sample when the sample is at a certain temperature or within a certain temperature range. The GUI 200 then provides a prompt 293 to the user, such as a prompt to insert the probe into the sample unit the probe opening (sample inlet) is submerged in the liquid (FIG. 24). Once the probe is submerged, the user can select the start button 211 to begin the test. The GUI 200 also presents results of the tests, such as results of a single test (FIG. 25), results of multiple tests (FIG. 26), results of a time test (FIG. 27), and results of a temperature test (FIG. 28). The results of the tests can be printed using button 215 and/or screen captured using button 213. The GUI 200 allows a user to configure one or more tests, such as entering a number of tests to be performed (FIG. 29), setting a duration of the test (FIG. 30), and setting a target temperature for a test (FIG. 31), each of which can be accepted by selecting button 217. The GUI 200 can present timed test results (FIG. 32). The GUI 200 also includes an export button 219 for exporting the test results, such as via a USB connection.

Examples and Design Considerations

Figure 33:
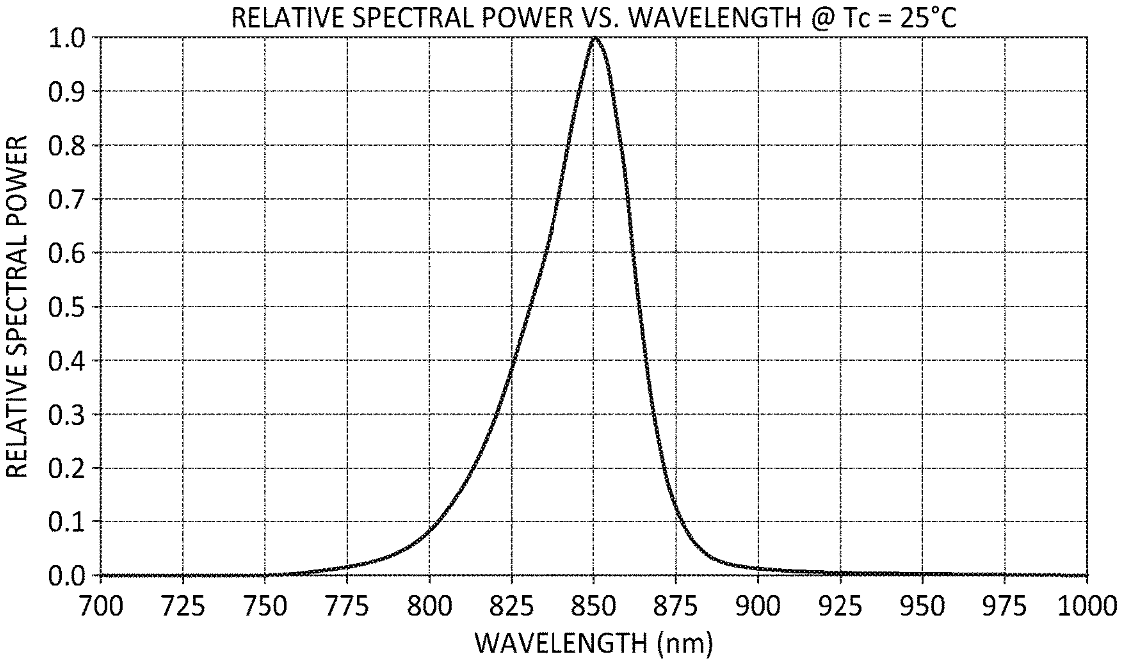
FIG. 33 is graph of LED spectrum power distribution in accordance with embodiments of the present disclosure.

In one example, a haze test can be performed with light that is an 850 nm wavelength (near IR) LED. FIG. 33 is a graph of an LED spectrum power distribution. In other embodiments, the light can be a different wavelength. The haze number is proportional to the light transmission efficiency. The measurements taken include both transmitted and scattered light. A color test can be performed based on CIE 1931 color testing standard. At first, the transmission color is computed as an XYZ value. Then, the XYZ value is fitted into an experimental model to be interpreted as three petroleum color standards. Each color standard is an eye observation conversion. The color standard also contains information on intensity transmission efficiency except for Platinum Cobalt, which does not have intensity information.

In existing systems, light transmits through a parallel glass (or plastic) and the sample at a current cuvette design. If the light is collimated (light transmitted in parallel), the refractive index of glass and sample will not play a role in the image at the detector end. If the light is not collimated, there is a lens effect to focus or diverse the light. The unevenness at the glass or liquid distance will create wavefront distortion to create an uneven image (varying light intensity) at the detector to cause measurement error. This error can occur on existing instruments for both haze and color testing. In contrast, in the present probe-based system, the light path is inside the liquid, eliminating the effect of two glass (or plastic) windows.

Figure 34:
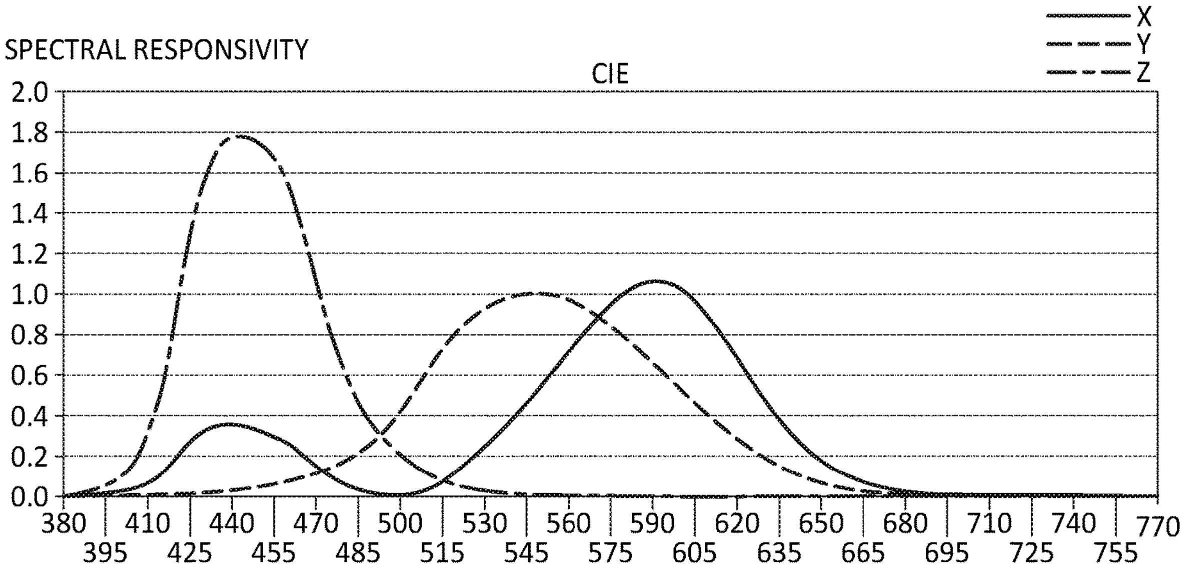
FIG. 34 is a graph of sensor spectrum response curve in accordance with embodiments of the present disclosure.

CMOS imaging sensors and light sensors were tested as an option for the detector. Light sensors with built-in wavelength filters (colors and near IR on one chip), AD at high resolution (16-bit), and standard serial communication (like I2C) were tested. One light sensor tested had both XYZ and near IR detection capabilities. A sensor with a specific wavelength can also be used for specific enhancement of color detection. At 16-bit on-chip AD, the sensor resolution can be at 1.5 ppm (0.0015%) of the full intensity. The chip can include an LED controller. An exemplary sensor spectrum response curve is shown in FIG. 34.

The system can be design such that both the light source and sensor have a stable electrical current to be able to achieve consistent measurements. The LED light can be controlled with PWM (Pulse Width Modulation-rapid switching on/off of the current) or constant current. At the PWM mode, flickering of the light source can occur if the modulation frequency is low. With a higher speed sensor, the frequency requirement will be higher. At the current mode, the light intensity is proportional to the current level and no flickering of the light was observed. The light sensor can have a built-in LED current controller.

Light propagation (image forming at the detector) is consider in the design. Existing instruments have a single element collimating lens in front of the light. A simple test showed that this existing collimating designs was not preferred. A strong lens effect at the haze and color testing was observed. In some embodiments, a collimated light (all in parallel) is used. A diffraction-limited collimating beam with two achromatic lenses and one microscope objective was formed to test this concept. The light beam travelled far without lens effect. The complexity of this design can be cost prohibitive. In another embodiment, a light guide approach can be used. LED light is affordable and can be used to produce substantial amounts of light. The light guide also allows all electrical components to remain above the sample liquid. The design of a light guide can be cost prohibitive. In other embodiments, a pinhole camera and LED illumination film (which provide diffuse, uniform light generation) can be used. The LED illumination film is a preferred embodiment of the light source, is cost-effective, and provides uniformly diffused illumination.

The system disclosed herein is described as a probe-based, parallel-light spectroscopy system to perform the measurements pursuant to, e.g. ASTM, Saybolt, & Cobalt color test routines, as well as haze in liquid samples. However, it would be apparent to one skilled in the relevant chemical, engineering, environmental science, or other technical art, that the system may be applicable to other environments, settings and applications.

The concepts disclosed in the present application can be combined with one or more of the concepts of U.S. Pat. No. 11,619,549 ('549 patent). The system disclosed herein can be used to perform the measurements that are performed by the system disclosed in the '549 patent.

The foregoing description has been presented for purposes of illustration and description of preferred embodiments. This description is not intended to limit associated concepts to the various systems, apparatus, structures, and methods specifically described herein. For example, system and methods described in the context of a probe or manual device or localized environments, may be applicable, in part or in entirety, to other measurement environments or tasks, such as field environments, long-haul trucks or similar powered mobile vehicles. The embodiments described and illustrated herein are further intended to explain the best and preferred modes for practicing the system and methods, and to enable others skilled in the art to utilize same and other embodiments and with various modifications required by the particular applications or uses.

The following exemplary "claims" are provided to set out and describe various aspects of the disclosure. The listing of claims is not intended to be limiting. It should be noted that elements described by the claims may take alternative forms, as may be described above, and various combinations may be implemented (including combinations not described by the dependencies in the claims). For example, the present disclosure extends to methods of operation of any of the systems or apparatus listed, including operation of any subsystem or combination of elements. The disclosure also extends to any system or apparatus described above suitable to perform any methods, process, or operation (and steps) listed below. Such combinations and alternative forms are well within the spirit and scope of the present disclosure.

Although the present embodiments and advantages have been described in detail, it should be understood that various changes, substitutions and alterations can be made herein without departing from the spirit and scope of the disclosure. Moreover, the scope of the present application is not intended to be limited to the particular embodiments of the process, machine, manufacture, composition of matter, means, methods and steps described in the specification. As one of ordinary skill in the art will readily appreciate from the disclosure, processes, machines, manufacture, compositions of matter, means, methods, or steps, presently existing or later to be developed that perform substantially the same function or achieve substantially the same result as the corresponding embodiments described herein may be utilized according to the present disclosure. Accordingly, the appended claims are intended to include within their scope such processes, machines, manufacture, compositions of matter, means, methods, or steps.

What is claimed is:

1. A method for in-situ measurement of optical properties of liquid samples using a handheld probe system, the method comprising:

obtaining a liquid sample, the liquid sample contained within a container;

providing a handheld probe system, the handheld probe system comprising a handheld housing and an elongated probe, the elongated probe having a first end coupled with the handheld housing, a second end extending from the handheld housing and spaced apart from both the first end and the handheld housing, a sample chamber that is a void space within the elongated probe between the first and second ends, and a sample inlet that is an opening into the void space;

manually manipulating the handheld housing to insert at least the second end of the elongated probe into the container while maintaining the handheld housing outside of a volume of the container and out of contact with the liquid sample, wherein the elongated probe is inserted into the container at least until the sample inlet and sample chamber are immersed within and surrounded by the liquid sample such that the sample inlet and sample chamber are in fluid communication with the liquid sample and such that a portion of the liquid sample flows freely into the void space;

directing a first light to a first light sensor along a first optical path, and determining a first intensity of the first light directed to the first light sensor;

with the void space in fluid communication with the liquid sample in the container, directing a second light along a second optical path, through the elongated probe, through the liquid sample within the sample chamber, and to a second light sensor, and determining a second intensity of the second light directed to the second light sensor; and determining a concentration of contaminant in the liquid sample including determining a difference in the first and second intensities.

2. A handheld probe system for in-situ measuring of optical properties of liquid samples, the system comprising:

a handheld housing;

at least one light source, a first light sensor, and a second light sensor, each positioned within the handheld housing;

an elongated probe extending from the handheld housing, wherein the elongated probe has a first end coupled with the handheld housing and a second end that extends from the handheld housing and is spaced apart from the first end and from the handheld housing;

a sample chamber, wherein the sample chamber is a void space within the elongated probe that is positioned between the first and second ends of the elongated probe;

a sample inlet, wherein the sample inlet is an opening into the void space of the sample chamber;

wherein the elongated probe is configured to be positioned within a target environment that contains a liquid sample such that the sample chamber and sample inlet are immersed within and surrounded by the liquid sample and such that the void space is in fluid communication with the liquid sample through the sample inlet and a portion of the liquid sample enters the void space via the sample inlet; and wherein the at least one light source is in optical communication with the first light sensor along a first optical path;

wherein the at least one light source is in optical communication with the second light sensor along a second optical path, and wherein the second optical path extends through the elongated probe and intersects with the void space.

3. A probe system for in-situ measuring of optical properties of liquid samples, the system comprising:

a housing;

at least one light source and at least one light sensor positioned within the housing;

an elongated probe extending from the housing, wherein the elongated probe has a first end coupled with the housing and a second end that extends from the housing and is spaced apart from the first end and from the housing;

a sample chamber, wherein the sample chamber is a void space within the elongated probe that is positioned between the first and second ends of the elongated probe;

a sample inlet, wherein the sample inlet is an opening into the void space of the sample chamber;

wherein the elongated probe is configured to be positioned within a target environment that contains a liquid sample such that the sample chamber and sample inlet are immersed within and surrounded by the liquid sample and such that the void space is in fluid communication with the liquid sample through the sample inlet and a portion of the liquid sample enters the void space via the sample inlet; and wherein the at least one light source is positioned to direct light through the elongated probe and into the sample chamber, and wherein the at least one light sensor is positioned to receive light from the sample chamber.

4. The system of claim 3, wherein the void space is sized and configured to draw a portion of the liquid sample into the void space.

5. The system of claim 3, wherein the at least one light source comprises a multi-wavelength light source;

the system comprising a collimator, wherein the multi-wavelength light source is positioned to direct light through the collimator; and the system comprising a beamsplitter, wherein the collimator is positioned to direct the light to the beamsplitter;

wherein the at least one light sensor comprises a first light sensor, wherein the beamsplitter is configured to direct the first light to the first light sensor;

wherein the at least one light sensor comprises a second light sensor positioned to detect the second light emitted from the sample chamber.

6. The system of claim 5, further comprising a return mirror positioned to reflect the second light from within the sample chamber back to the beamsplitter, wherein the beamsplitter is configured to direct the second light from the sample chamber to the second light sensor.

7. The system of claim 6, wherein the return mirror is configured such that at least some of the second light passes through the liquid sample in the sample chamber at least twice prior to detection by the second light sensor.

8. The system of claim 5, wherein the first light sensor measures the first intensity of the first light emitted from the multi-wavelength-light source, and wherein the second light sensor measures the second intensity of the second light after passing through liquid sample within the sample chamber.

9. The system of claim 6, further comprising a first folding mirror positioned between the beamsplitter and the first light sensor and arranged to direct the first light to the first light sensor, and a second folding mirror positioned between the beamsplitter and the second light sensor and arranged to direct the second light to the second light sensor.

10. The system of claim 3, wherein the elongated probe is configured to fit within and extend into a cavity of a container that contains the liquid sample, and wherein the housing is configured to rest on and remain outside of the cavity of the container.

11. The system of claim 3, further comprising a scatter sensor positioned within the elongated probe between the first and second ends, wherein the scatter sensor is configured to detect light scattered within the sample chamber.

12. The system of claim 3, further comprising a temperature sensor positioned within the elongated probe between the first and second ends, wherein the temperature sensor is configured to measure a temperature of the liquid sample within the sample chamber.

13. The system of claim 3, wherein the sample chamber is configured to receive the liquid sample through the sample inlet when the elongated probe is inserted into the liquid sample.

14. The system of claim 13, wherein the system is configured to measure the optical properties of the liquid sample while the probe is inserted into the liquid sample.

15. The system of claim 14, wherein the optical properties comprise haze, color, or combinations thereof.

16. The system of claim 3, further comprising a computer and software in the housing, wherein the software is configured to determine a light-absorbing intensity of the liquid sample by comparing intensity, as a function of wavelength, of the first light transmitted to and measured by a first light sensor of the at least one light sensor to intensity, as a function of wavelength, of the second light transmitted to and measured by a second light sensor of the at least one light sensor.

17. The system of claim 3, further comprising a graphical user interface on the housing including controls configured to allow a user to select and initiate a test of the liquid sample and view test results of a test of the liquid sample.

18. A method for in-situ measurement of optical properties of liquid samples, the method comprising:

providing an elongated probe, the elongated probe having a first end, a second end, a sample chamber that is a void space within the elongated probe between the first and second ends, and a sample inlet that is an opening into the void space;

inserting at least the first end of the elongated probe into a target environment, the target environment containing a liquid sample, wherein the elongated probe in inserted into the target environment at least until the sample inlet and sample chamber are immersed within and surrounded by the liquid sample such that the sample inlet and sample chamber are in fluid communication with the liquid sample and such that a portion of the liquid sample flows into the void space;

directing a first light to a first light sensor;

with the void space in fluid communication with the liquid sample in the target environment, directing a second light through the elongated probe and through the liquid sample within the sample chamber;

with the void space in fluid communication with the liquid sample in the target environment, directing at least some of the second light that has passed through the liquid sample within the sample chamber from the sample chamber to a second light sensor;

determining a first intensity of the first light directed to the first light sensor;

determining a second intensity of the second light directed to the second light sensor; and determining a difference in the first and second intensities and correlating the difference to a concentration of contaminant in the liquid sample.

19. The method of claim 18, wherein inserting the void space into the liquid sample draws a portion of the liquid sample into the void space via displacement, and wherein the void space is maintained in equilibrium with a volume of the liquid sample in the target environment such that the liquid sample flows between the void space and the target environment during the directing of the second light.

20. The method of claim 18, wherein the determining and the correlating comprises determining a haze of the liquid sample including determining an instrument haze rating and a haze clarity index of the liquid sample.

21. The method of claim 18, wherein the directing of the first and second lights comprises directing an initial light from a multi-wavelength light source through a collimator and to a beamsplitter, wherein the beamsplitter splits the initial light to form the first light and the second light;

wherein the first light is directed from the beamsplitter to the first light sensor;

wherein the second light is directed from the beamsplitter and through the liquid sample in the sample chamber.

22. The method of claim 18, wherein the intensities of the first and second lights are determined without removal of the liquid sample from the target environment and while the elongated probe is immersed in the liquid sample.

23. The method of claim 18, wherein the portion of the liquid sample that enters the void space of the sample chamber via the sample inlet is less than an entirety of the liquid sample in the target environment.

24. The method of claim 18, wherein the portion of the liquid sample that enters the void space via the sample inlet is not isolated from a remainder of the liquid sample in the target environment.

25. The method of claim 18, wherein the path of the second light traverses through the portion of the target environment that coincides with the void space.

* * * * *